United States Patent
Taylor et al.

(10) Patent No.: US 11,471,402 B2
(45) Date of Patent: Oct. 18, 2022

(54) HYDROGEL-BASED BIOLOGICAL DELIVERY VEHICLE

(71) Applicant: InSitu Biologics, Inc., Saint Paul, MN (US)

(72) Inventors: William Taylor, Woodbury, MN (US); Daniel Sipple, Saint Paul, MN (US); James Segermark, Saint Paul, MN (US)

(73) Assignee: INSITU BIOLOGICS, INC., Woodbury, MN (US)

( * ) Notice: Subject to any disclaimer, the term of this patent is extended or adjusted under 35 U.S.C. 154(b) by 0 days.

(21) Appl. No.: 16/300,660

(22) PCT Filed: May 12, 2017

(86) PCT No.: PCT/US2017/032406
§ 371 (c)(1),
(2) Date: Nov. 12, 2018

(87) PCT Pub. No.: WO2017/197262
PCT Pub. Date: Nov. 16, 2017

(65) Prior Publication Data
US 2019/0175495 A1    Jun. 13, 2019

Related U.S. Application Data

(60) Provisional application No. 62/335,457, filed on May 12, 2016.

(51) Int. Cl.
| | | |
|---|---|---|
| A61K 9/00 | (2006.01) | |
| A61K 47/36 | (2006.01) | |
| A61K 9/06 | (2006.01) | |
| A61K 31/327 | (2006.01) | |
| A61K 31/738 | (2006.01) | |
| C12N 9/08 | (2006.01) | |

(52) U.S. Cl.
CPC .......... *A61K 9/0024* (2013.01); *A61K 9/0019* (2013.01); *A61K 9/06* (2013.01); *A61K 31/327* (2013.01); *A61K 31/738* (2013.01); *A61K 47/36* (2013.01); *C12N 9/0065* (2013.01); *C12Y 111/01007* (2013.01)

(58) Field of Classification Search
CPC ...... A61K 9/0024; A61K 9/0019; A61K 9/06; A61K 31/327; A61K 31/738; A61K 47/36; C12N 9/0065; C12Y 111/01007
See application file for complete search history.

(56) References Cited

U.S. PATENT DOCUMENTS

| | | | |
|---|---|---|---|
| 5,258,042 A | 11/1993 | Mehta | |
| 6,372,494 B1* | 4/2002 | Naughton | A61K 35/36 435/391 |
| 7,368,502 B2 | 5/2008 | Calabro et al. | |
| 7,465,766 B2 | 12/2008 | Calabro et al. | |
| 8,021,350 B2 | 9/2011 | Calabro et al. | |
| 8,124,120 B2* | 2/2012 | Sadozai | A61K 9/0021 424/426 |
| 8,137,688 B2 | 3/2012 | Calabro et al. | |
| 8,138,265 B2 | 3/2012 | Zahos et al. | |
| 8,207,262 B2 | 6/2012 | Calabro et al. | |
| 8,410,180 B2 | 4/2013 | Calabro et al. | |
| 2008/0274161 A1* | 11/2008 | Muratoglu | B01J 13/0065 424/425 |
| 2009/0186077 A1 | 7/2009 | Ying et al. | |
| 2009/0252700 A1* | 10/2009 | Zahos | C08L 5/08 424/78.17 |
| 2010/0074956 A1* | 3/2010 | Kurisawa | C12Q 1/28 424/486 |

(Continued)

FOREIGN PATENT DOCUMENTS

| | | |
|---|---|---|
| JP | 2011-522817 A | 8/2011 |
| WO | 2004063388 A2 | 7/2004 |

(Continued)

OTHER PUBLICATIONS

Petr Snetkov. Hyaluronic acid. Polymers & Plastics | Biochemistry. 12 pages (encyclopedia.pub/2492). (Year: 2020).*
F. Lee et al. / Journal of Controlled Release 134 (2009) 186-193 (Year: 2009).*
Hebeish et al. Novel nanocomposite hydrogel for wound dressing and other medical applications. RSC Adv., 2015, 5, 103036-103046. (Year: 2015).*
Sadeghi. Synthesis of a Biocopolymer Carrageenan-g-Poly(AAm-co-IA)/Montmorilonite Superabsorbent Hydrogel Composite. Brazilian Journal of Chemical Engineering, 2012, 29(02):295-305. (Year: 2012).*
Cates. Influence of Crosslink Density on Swelling and Conformation of Surface-Constrained Poly(N-Isopropylacrylamide) Hydrogels. University of South Florida. Thesis. 2010, 96 pages. (Year: 2010).*

(Continued)

*Primary Examiner* — Robert A Wax
*Assistant Examiner* — Olga V. Tcherkasskaya
(74) *Attorney, Agent, or Firm* — Dentons Davis Brown, P.C.; Matthew W. Coryell

(57) ABSTRACT

A hydrogel-based biological delivery vehicle used to effectively deliver drug and biological material to tissue or organ sites. More specifically, a hydrogel binding matrix having a biopolymer backbone containing carboxyl groups. Tyramine may be substituted for at least a portion of the carboxyl groups, so that, when hydrogen peroxide is added, it causes creation of covalent bonds between tyramine molecules and cross-links the hydrogel binding matrix, thereby enabling the hydrogel binding matrix to transition from liquid to gel state. The hydrogel binding matrix, in its liquid form, is capable of encapsulating drug reservoirs to create a homogenous liquid with evenly distributed particles containing drugs or target molecules. As the hydrogel binding matrix solidifies into a gel state, the newly created cross-links do not disrupt or react with the drugs or target molecules contained within the drug reservoirs. This hydrogel-based biological delivery vehicle can be used in several medical applications.

16 Claims, 7 Drawing Sheets

(56) References Cited

U.S. PATENT DOCUMENTS

| | | | |
|---|---|---|---|
| 2011/0166417 A1* | 7/2011 | Lin | F01N 13/08 600/104 |
| 2012/0100103 A1* | 4/2012 | Park | A61L 27/52 424/85.2 |
| 2015/0050332 A1 | 2/2015 | Schubert | |

FOREIGN PATENT DOCUMENTS

| | | | |
|---|---|---|---|
| WO | 2006010066 A2 | 1/2006 | |
| WO | 2009102967 A2 | 8/2009 | |
| WO | 2011037349 | 3/2011 | |
| WO | WO-2011037349 A2 * | 3/2011 | A61K 47/36 |

OTHER PUBLICATIONS

Chun-Shu Wei, Chul Kim, Hyun-Je Kim, Praopim Limsakul; Hydrogel Drug Delivery: Diffusion Models Thesis; 2012; 23 pp.

Enrica Calo, Vitaliy V. Khutoryanskiy; Biomedical applications of hydrogels: A review of patents and commercial products; Journal Article; 2014; 17 pp.; European Polymer Journal.

Billard et al., "Liposome-loaded chitosan physical hydrogel: Toward a promising delayed-release biosystem", "Carbohydrate Polymers", Sep. 30, 2014, pp. 651-657, vol. 115, Publisher: Applied Science Publishers, Ltd., Published in: Barking, GB.

Grijalvo et al., "Biodegradable liposome-encapsulated hydrogels for biomedical applications: a marriage of convenience", "Biomaterials Science", Jan. 1, 2016, pp. 555-574, vol. 4, No. 4.

Park et al, "Macro/Nano-Gel Composite as an Injectable and Bioactive Bulking Material for the Treatment of Urinary Incontinence", "Biomacromolecules", May 2, 2014, pp. 1979-1984, vol. 15, No. 6.

Widjaja et al., "Hyaluronic acid-based nanocomposite hydrogels for ocular drug delivery applications", "Journal of Biomedical Materials Research", Oct. 9, 2013, vol. 102, No. 9, Published in: Hoboken, NY.

Xu et al., "Hyaluronidase-incorporated hyaluronic acid-tyramine hydrogels for the sustained release of trastuzumab", "Journal of Controlled Release", Aug. 7, 2015, vol. 216, Published in: Amsterdam, NL.

* cited by examiner

Types of Hydrogel Reservoirs

Elution Rate for Each Reservoir Type

Overall Elution Rate

HYDROGEL-BASED BIOLOGICAL DELIVERY VEHICLE

CROSS-REFERENCE TO RELATED APPLICATION

This application claims the benefit of U.S. Provisional Application No. 62/335,457, filed May 12, 2016 titled HYDROGEL-BASED BIOLOGICAL DELIVERY VEHICLE.

FIELD OF THE INVENTION

This disclosure relates to a delivery system hydrogel binding matrix used to effectively deliver drug and biological material formulations. More specifically, it relates to a hydrogel matrix that creates cross-links when it transitions from liquid to gel state. The hydrogel matrix, in its liquid form, is capable of encapsulating drug reservoirs to create a homogenous liquid with evenly distributed drug reservoirs containing one or more drugs or target molecules. As the binding matrix (i.e., hydrogel having evenly distributed drug reservoirs) solidifies into a gel state, it creates cross-links that do not disrupt or react with the one or more target drugs or molecules contained within the drug reservoirs. This hydrogel-based biological delivery vehicle can be used in a variety of medical applications.

BACKGROUND OF THE INVENTION

Hydrogels have become popular in medical application for several reasons. To form them, frequently they need to be cross-linked using free-radical generating compounds or other radiation. However, this results in residual material that needs to be removed due to its potentially dangerous effects to the receiving subject. Additionally, drugs or medications are usually added to a hydrogel through passive diffusion or by using thermal treatment or irradiation. These are not ideal ways to load hydrogels, though, because passive diffusion results in low concentrations of the drugs or medications, and thermal treatment or irradiation often cause drug agents to react with the hydrogel or damage or inactivate biological agents.

Liposome formulations are often dilute and have a viscosity relatively close to water. When used as a drug delivery vehicle, the liposome formulations can easily extrude back out of the injection site or drain away from targeted tissues through the interstitial spaces and carry the drug or target molecule away from the targeted site. Liposomes sometimes have unpredictable stability. For example, they may release the target molecule too quickly if they coalesce and quickly break apart or, if they are sufficiently dilute, they may remain stable and prevent the target molecule from being delivered to the target tissue in a timely fashion. Other forms of alternative drug delivery vehicles or drug reservoirs also exist, such as dense hydrogel particles or porous particles. However, particles also migrate after injection or placement and are prone to aggregating in one spot.

Therefore, a solution is needed that enables a hydrogel to cross-link without creating residual material, that promotes higher level of drug/medication concentration loading, that does not react with or deactivate drugs/medications loaded into the hydrogel, and that enables drug delivery vehicles, also referred to as drug reservoirs, to have more stability and to release at a predictable rate in a desired location.

SUMMARY OF THE INVENTION

The disclosed hydrogel-based biological delivery vehicle is a delivery system comprised of drug reservoirs that encapsulate drugs or target molecules, and a hydrogel matrix that, when used to hold the drug reservoirs in place is referred to as a binding matrix. The binding matrix disclosed herein acts as a support to keep drug reservoirs dispersed evenly throughout the delivery system when it is implanted in or on a subject. The binding matrix does not significantly hinder diffusion and elution of the active target molecule from the drug reservoir. According to one embodiment, the desired hydrogel formulation can be adjusted to impact diffusion of the target molecule and increase or decrease the elution rate.

More specifically, the delivery system disclosed herein addresses problems with liposome formulation stability and release by allowing the liposome formulation to be encapsulated within a liquid formation of a binding matrix before cross-linking occurs. This creates a homogenous liquid with liposomes thoroughly mixed throughout. Once mixed, the relatively gentle reaction conditions that create cross-links within the hydrogel matrix do not disrupt the liposomes or react with the liposome components or the drugs or target molecules that are contained within the liposomes.

The delivery system disclosed herein also addresses problems with entrained particle formulation release by suspending and evenly dispersing the particles throughout the binding matrix and retaining them in place relative to each other. This allows for even and predictable elution of the drug from the particles after injection or placement of the delivery system into a specific delivery site. Whereas the liposome elution depends on a physical separation of the target molecule from its surroundings with a lipid bilayer, the particles elute target molecules depending on diffusion from the particle. Diffusion is dependent upon the target molecule's affinity for the particle material, the path tortuosity, osmotic changes within and at the particle boundary, and chemical potential and the resulting chemical gradient. Sometimes a phase change can be a limiting step if the target molecule has to first dissolve into the surrounding fluid.

Mixtures of multiple types of hydrogel consistency can be used to create various rates of drug delivery and, therefore, various delivery times of the target molecules. The hydrogel matrix can be formulated to range from a thicker liquid consistency to a hard, solid, gelatin particle. The hydrogel matrix's consistency impacts the degree of degradation of the hydrogel matrix and, therefore, the speed of release from the delivery system and delivery of the drugs or target molecules to the targeted tissues. For particle formulations, the hydrogel degradation allows the particles to come into direct contact with the tissues and allows the particles to be absorbed by the body after the drug has been dispensed. Particles may be comprised of protein scaffolds that promote healing and regrowth.

In some embodiments, the thick nature of the hydrogel matrix composition can allow the delivery vehicle (i.e., the drug reservoirs) to coat tissues and stay in place within those tissues so as to ensure the targeted site is the resulting location of drug delivery. If the hydrogel matrix formulation is sufficiently concentrated and highly cross-linked it could impact elution and absorption rates.

DETAILED DESCRIPTION

Figure 1:
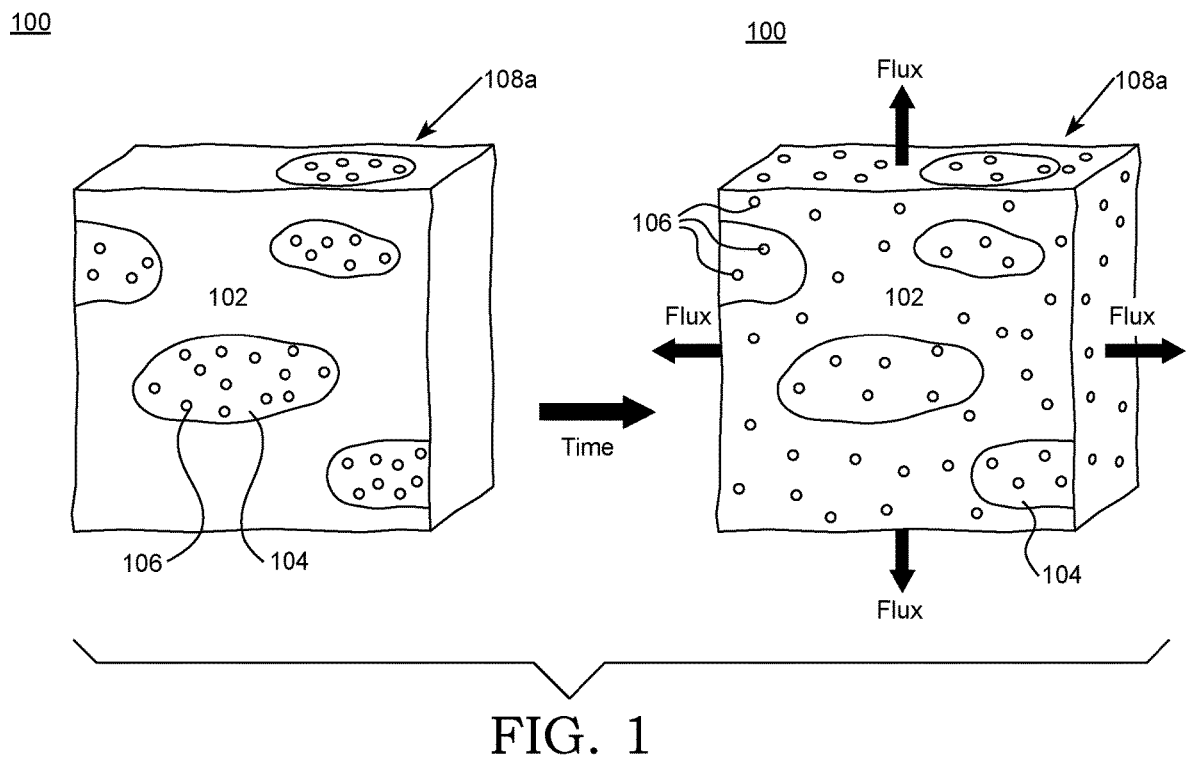
FIG. 1 illustrates molecules eluting from drug reservoirs within one embodiment of the disclosed delivery system.

The present disclosure relates to biological delivery vehicle that is used to effectively deliver drugs and target molecules to specific tissue sites. Various embodiments of the biological delivery vehicle will be described in detail with reference to the drawings, wherein like reference numerals represent like parts and assemblies throughout the several views. Reference to various embodiments does not limit the scope of the biological delivery vehicle disclosed herein. Additionally, any examples set forth in this specification are not intended to be limiting and merely set forth some of the many possible embodiments for the biological delivery vehicle. It is understood that various omissions and substitutions of equivalents are contemplated as circumstances may suggest or render expedient, but these are intended to cover applications or embodiments without departing from the spirit or scope of the disclosure. Also, it is to be understood that the phraseology and terminology used herein are for the purpose of description and should not be regarded as limiting.

The disclosed hydrogel-based biological delivery vehicle is a delivery system 100 comprised of drug reservoirs 104 that encapsulate drugs or target molecules 106, and a hydrogel matrix that, when used to hold the drug reservoirs 104 in place is referred to as a binding matrix 102.

Generally, the biological delivery vehicle disclosed in this application is a delivery system 100 comprised of drug reservoirs 104 that encase and protect a drug or target molecule 106 and that are suspended in a hydrogel matrix that, when used to hold the drug reservoirs in place is referred to as a binding matrix 102. The drug reservoir 104 may be, for example, a dense hydrogel particle, a porous particle, a liposome, a cellulosic particle, the drug itself in a crystalline or solid phase that dissolves when eluting out of the delivery system 100, or a protein fragment, which because of its association with tyrosine would like be in a cellulose or liposome drug reservoir 104 instead of a tyramine-substituted dense hydrogel particle. The process of creating the delivery system 100 generally involves associating the drug reservoir 104 with the drug or target molecule 106 and mixing the combination into a pre-cross-linked, liquid hydrogel matrix (for example, a tyramine-substituted sodium hyaluronate, wherein a predetermined percent of carboxyl groups in the sodium hyaluronate are substituted out for tyramine) that is then cross-linked (for example, by adding hydrogen peroxide to create covalent bonds between tyramine molecules) to create the final binding matrix 102. This cross-linking occurs in the presence of a drug or target molecule 106 and, beneficially, does not create a harsh reaction condition or cause a reaction with the drug or target molecule 106. The delivery system 100 can then be injected or placed on or at the desired delivery site 108a, and the drug elutes at a predetermined rate based on the density of the binding matrix 102 and the specific drug reservoir 104 used.

Liposomes are one example of a drug reservoir 104. They are spherical vesicles with at least one lipid bilayer surrounding an aqueous inner solution. They are primarily used as a vehicle to deliver drugs or other target molecules 106 to a target site 108a in a biological system. There are several different kinds of liposomes and they range in size, from small to large, as well as in layers, from a single bilayer to multilamellar vesicles (i.e., liposomes having multiple lipid bilayers). Liposomes are usually prepared by mixing the aliphatic, amphipathic molecules with polar solvents and target molecules and then sonicating, extruding, or placing the mixture under shear conditions.

This disclosure relates to a biological delivery vehicle (i.e., a delivery system 100) created by entraining a useful drug reservoir 104 into a binding matrix 102 to stabilize and control drug delivery rate. In some embodiments, liposomes are the preferred delivery vehicle 104 because they can protect highly reactive drugs or target molecules 106 (ex. toxin, antibodies, large macromolecules, etc.) from reaction with the hydrogel matrix. However, these drugs or target molecules 106 may aggregate within the liposome. Therefore, other drug reservoirs 104 are considered and disclosed.

Generally, drug reservoirs 104 containing drugs, proteins, biological molecules and/or targeted materials/molecules 106 are encapsulated into a hydrogel matrix that is cross-linked to form a binding matrix 102 containing the drug reservoirs 104. The binding matrix 102 allows the drug reservoirs 104 to be encapsulated within the liquid formulation prior to cross-linking and does not require a purification step after cross-linking occurs. The gentle cross-linking reaction does not compromise or react with the drug reservoirs 104 or the target molecules 106 contained within them.

During placement of a delivery system 100 into targeted biological tissues 108a, the drug reservoirs 104 in the binding matrix 102 are stabilized and held in place relative to each other by the surrounding cross-linked hydrogel material, as illustrated in FIG. 1. After a pre-determined amount of time, the binding matrix 102 is broken down and absorbed by the surrounding tissues, and the drug reservoirs 104 and the target molecules 106 in the drug reservoirs 104 are released to the neighboring tissues 108a via passive diffusion, as illustrated in FIG. 1. This allows for the more predictable and reproducible delivery of the drug reservoirs 104 and their molecular cargo 106 to the targeted biological tissues 108a.

In addition to passive diffusion, wherein the drugs and target molecules 106 elute from the drug reservoirs 104, through the binding matrix 102 and out into the surrounding tissue 108a, second or third order diffusion may take place. More specifically, after the delivery system 100 is placed on, in, or near the tissue site 108a, the binding matrix 102, which has a higher osmolality than the surrounding tissues 108a, will absorb water from the surrounding tissue 108a (which slows elution rates) and break into smaller particles with increased surface areas. The increase in surface area causes elution rates to then increase because of the increased surface area to volume ratio. Therefore, over time, the elution rate may increase.

Figure 2:
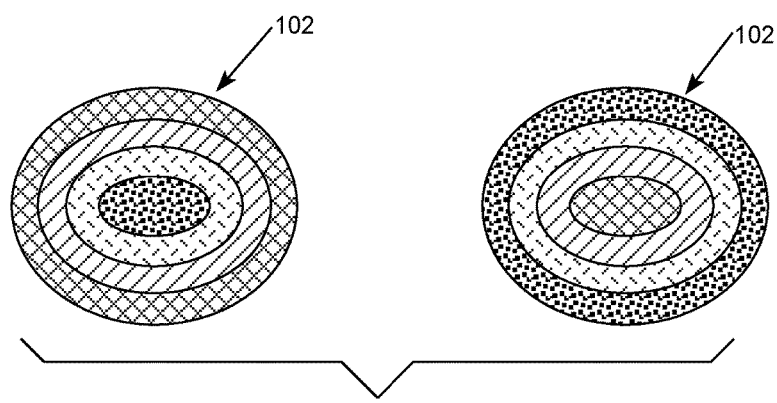
FIG. 2 illustrates types of hydrogel reservoirs having variable densities of hydrogel matrix.

In some embodiments, layers of differing hydrogel density may be used to create the binding matrix 102, as illustrated in FIG. 2. Since hydrogel that is less dense enables faster elution rates, by using layers of differing hydrogel density, the elution rate can be further controlled. In one example, the binding matrix 102 may have its most dense material in the middle, with each successive layer being less dense than the prior layer. In another example, the binding matrix 102 may have its least dense material in the middle, with each successive layer being more dense than the prior layer.

In one embodiment, when at least some of the drug reservoirs 104 to be used in combination with the binding matrix 102 are dense hydrogel particles, the dense hydrogel particles are first prepared by solubilizing the drug or target molecule 106 in a pre-cross-linked, liquid hydrogel matrix. In some embodiments, the pre-cross-linked, liquid hydrogel matrix may include a predetermined percentage of tyramine-substituted sodium hyaluronate (hereinafter "THA") combined with an enzyme (for example, horseradish peroxidase). After the drug or target molecule 106 is added to the THA and enzyme mixture, a cross-linking agent, such as hydrogen peroxide, can be added to the hydrogel matrix to encourage cross-linking and solidification of the formulation, therefore binding the drug or target molecule 106 in place. The outcome from this procedure is the formation of dense hydrogel particles that can be ground and sized to a uniform particle diameter.

The advantage to sizing the dense hydrogel particles is to create particles of desired surface area to volume ratio that can be used to control steady elution rates. For example, by completing the above-described procedure a plurality of times so that a mixture of dense hydrogel particles with various densities and various surface area to volume ratios are created, the varied particles can be mixed together so that, in a final formulation, illustrated in FIG. 3A, the individual elution rates may vary, as illustrated in FIG. 3B, but the overall elution rate can be made constant at a controlled elution rate for a desired length of time, thereby providing a flat elution curve, as illustrated in FIG. 3C.

Figure 3A:
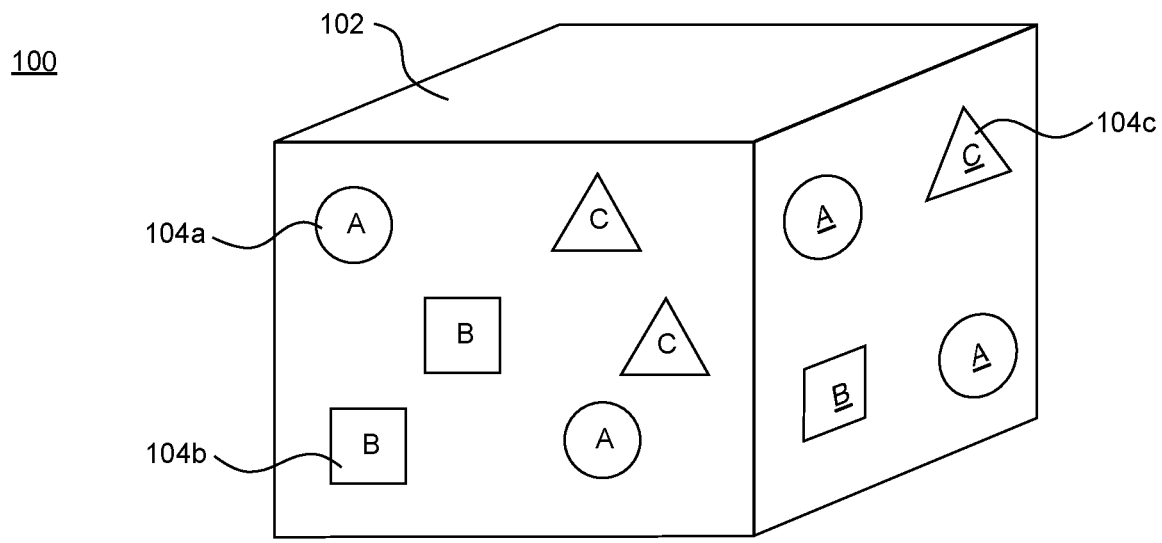
FIG. 3 illustrates the individual and overall elution rates for a delivery system having multiple drug reservoirs that elute molecules at different rates.
Figure 3B:
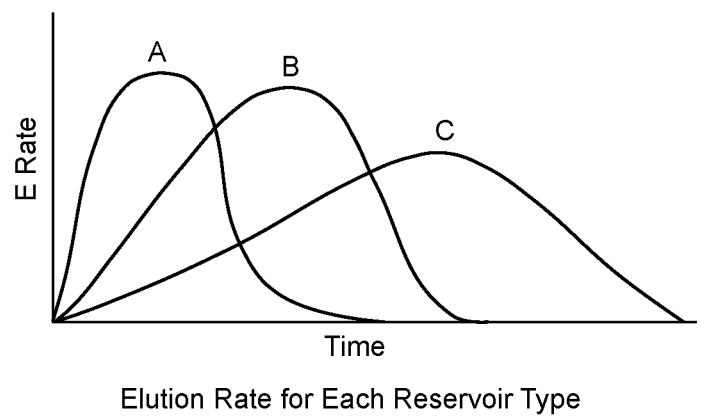
Figure 3C:
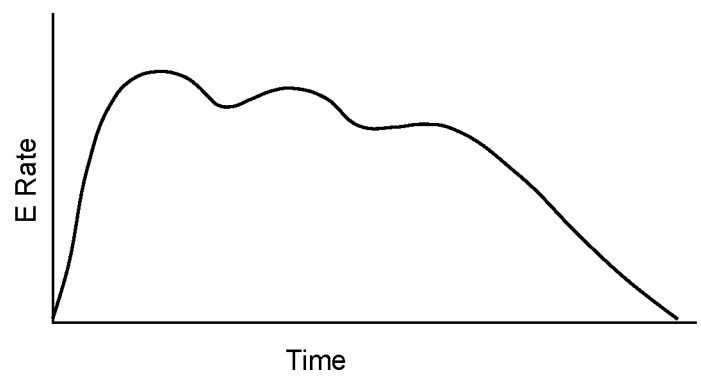

Therefore, after the dense hydrogel particles of one or more diameters are created, they are mixed into a hydrogel-based binding matrix 102, as illustrated in FIGS. 1 and 3A. The hydrogel matrix may be similar in formulation to the dense hydrogel particle formulation, but thinner and, therefore, able to dissolve faster once placed in, on, or near a targeted tissue 108a. The dense hydrogel particles can be mixed into the binding matrix 102 at a desired volume matrix to volume particle ratio to further control total elution and dose. If desired, the density of the binding matrix 102 can be changed to affect elution rate from the entire delivered volume.

For use of porous particles as drug reservoirs 104 to place desired drugs or target molecules 106 into targeted biological tissues 108a, the porous particles, which may be polymers and are porous in nature, are first loaded with the desired drug or target molecule 106 and, thereafter, either loaded directly into the hydrogel matrix as is or mixed with porous materials of various porosity, surface area, and loading. In a preferred embodiment, the desired drug or target molecule 106 is in the pores of the porous particle and the surrounding target tissues 108a can absorb the porous particles. In addition to liposomes, dense hydrogel particles, and porous particles, other hydrogels or water-soluble polymers, such as cellulosic particles, can be used to create the drug reservoir 104 prior to binding in the hydrogel matrix. Alternatively, the crystalline or solid phase form of a drug or target molecule 106 may be directly added to the binding matrix 102 and a drug reservoir 104 may not be used.

The binding matrix 102 can be modified to be thicker or thinner for application and to stay in position at the target biological tissues 108a. More specifically, the degree of cross-linking and composition can be designed to allow the binding matrix 102 to break apart at a desired rate, which optimizes target molecule delivery to the biological tissues 108a from the drug reservoirs 106. For example, a binding matrix 102 with a high degree of cross-linking will take longer to degrade and can enable the delivery system 100 (if injected) and, therefore, the drugs or medications 106 in the drug reservoir 104 to take more time in getting to and remaining in the targeted tissue area 108a.

In some embodiments, the disclosed delivery system 100 allows placement of high concentrations of target drugs and molecules 106 within desired tissue sites 108a that can be eluted from the placed mass at a desired rate. For example, an analgesic material added to a delivery system 100 using the above-described methods can be placed in relatively high concentration in a surgical site and elute out at a desired rate to treat pain post surgery. The delivery system 100 can be designed to elute the analgesic over a several day period, and this may prevent pain syndromes from developing and may allow the patient to recover faster and return home sooner.

Another example is the use of systemically toxic compounds (i.e. bupivacaine (cardiotoxic)) that could be released within the tissue 108a over a desired treatment time. A high concentration of a systemically toxic compound could, using other methods of delivery, elicit a systemic effect if given systemically over the same period in a concentration effective enough to treat the condition.

Similarly, a chemo toxic agent could be supplied from the mass in locally relatively high concentration that would impact fast growing cells nearby (i.e. tumors), but that will not impact the entire biological system in the same way. This results in fewer chemotherapy symptoms for the patient, yet creates locally high concentration of the chemotoxic agent making it more effective.

In another example, loading the drug reservoirs 104 with endotoxins/pyrogens or cytokines can elicit a locally large immune response, which may activate the patient's immune system to recognize a cancer near the placed delivery system 100 as foreign and attack the tumor cells. Interleukin-2 or other, similar immune system activators could also be used to elicit a similar response.

Overview of Hydrogel Composition and Use Cases

Hydrogel Composition: Overview

In some embodiments, the hydrogel matrix is comprised of a biopolymer backbone containing carboxyl chemical functional groups. Examples of biopolymer backbone include sodium hyaluronate and proteins. The carboxyl groups may be reacted with tyramine to create 0.5% to 5.0% substitution of the carboxyl groups with tyramine molecules, but could theoretically be created at lower (for example, 0.1%) and higher (for example, 7.0%) substitutions, wherein the percentage of substitution indicates the percent of tyramine substitutions made in relation to the number of carboxyl groups available to be substituted. In addition to a desired substitution rate, preferred embodiments of the hydrogel matrix have a desired THA concentration. More specifically, preferred embodiments of the binding matrix 102 are comprised of 1.0-5.0% concentration of THA (i.e., 1.0-5.0% THA in water) with tyramine substitutions at or below 1.5%. Preferred embodiments of the dense hydrogel particles include a concentration (i.e., percentage of THA in water) over 5% (i.e., 15-20%).

More specifically, in some embodiments, THA is placed into solution with the drug reservoir mixture 104 in the solvent phase. In the examples used in this disclosure, solutions containing up to 20% THA are the preferred concentration. In some cases where the liposomes are substituted with dense hydrogel particles or mixtures of particles of varying consistency, or where the mixture contains both liposomes and dense particles to control delivery rates of target molecules, dense particles could be approximately 5.5% tyramine substitution and, while usually up to 20% biopolymer (such as sodium hyaluronate) backbone, in some embodiments, greater than 20% biopolymer backbone.

The following brief examples and descriptions further explain how the basic concept of using a the disclosed delivery system 100 to effectively deliver drugs and target molecules 106 can be used in various additional medical applications, as described below.

Use Case: Overview of Plasma Protein Binder Complement

Acetaminophen, ibuprofen, and other small molecules can be incorporated into the drug reservoirs 104 in combination with a powerful analgesic to improve pharmacological response to the nearby tissues. Acetaminophen preferentially binds to plasma proteins and allows the powerful analgesic to impart a nociceptive response at lower concentrations. The use of a dense hydrogel particle or porous particle in a binding matrix 102, as opposed to liposomes, allows the main drug to last longer and have an effect at a lower concentration.

Use Case: Overview of Immune Stimulation in Cancer Treatment

The drug reservoirs 104 disclosed herein can be loaded with immune system stimulators such as, but not limited to, interleukin-2, other cytokines, etc. The localized strong immune response could create a response to tumor tissue located next to the implanted delivery system 100 and act as an effective treatment to the tumor or other target tissue 108a.

Use Case: Overview of Chemotoxic Cancer/Abnormal Tissue Growth Treatment

Chemotoxic agents can be encapsulated within the drug reservoirs 104 and then used to create a delivery system 100 that can be delivered to target tissues to kill undesired benign or non-cancerous growths, or used to target cancerous tissues. Localized placement of chemotoxic agents would dramatically decrease systemic effects and reduce symptoms from exposure to chemotoxic agents, but also maintain a medically effect dose of chemotoxic agents close to the target tissue or tumor 108a. This application could be used for solid tumor treatment, fibroids, prostrate, keratin growths, etc. A continuous exposure to an eluting chemotoxic material near the target tissue site 108a would ensure the cells are not able to repair themselves and survive treatment. One reason this is beneficial is because many times during treatments that use chemotoxic materials, the systemic impact is the limiting factor in treating difficult tumors. Maximizing target tissue exposure while minimizing systemic exposure is the novel concept demonstrated by the disclosed delivery system 100.

Use Case: Overview of Radiation, Radiofrequency, Microwave Treatment of Target Tissues and Tumors In some embodiments, target molecules can be delivered locally to target cells or tumors 108a for follow up radiation, radiofrequency, proton, or antibody treatment. Metal particles or ions can be concentrated in the drug reservoirs 104, which can then be added to the hydrogel matrix to create a delivery system 100. The delivery system 100 having metal particles or ions can then be injected within or near the target tumor 108a. Once irradiated, secondary radiation scattering can enhance the treatment. Although artificial gamma radiation is lower in energy than galactic cosmic rays, it could be enhanced by creating secondary scattering due to metals such as tantalum that could be placed into the target tissue 108a. However, while the targeted tumor 108a would be affected by this treatment, metal present in the delivery system 100 on the backside of the tumor during a proton beam treatment may shield tissues behind the delivery system 100. Finally, metal materials present in the delivery system 100 could be excited by radiofrequency irradiation and could create a localized hot spot that could thermally kill the target tissue or tumor 108a.

The above-described delivery system 100 and use cases are brief examples of the disclosed technology. Below is more detail regarding the hydrogel binding matrix 102, drug reservoirs 104, usable drugs and target molecules 106, and various beneficial uses of final delivery systems 100.

Tyramine Cross-Linked Biopolymer: Chemistry

As described above, part of the hydrogel matrix formulation can include tyramine cross-linked biopolymers. These biopolymers may have a specific chemical makeup that includes glycosaminoglycans, tyramine cross-linked polyamino acids, tyramine-substituted cross-linked molecules normally having a carboxyl functional group, a specific percent substitution of tyramine for the carboxyl groups, a specific cross-linking mechanism, a specific concentration of cross-linked biopolymers in water, and/or may include copolymers. Two main forms of the biopolymer are envisioned wherein both forms are based on a binding matrix 102 having a tyramine-based cross-linking mechanism: a tyramine-substituted sodium hyaluronate (HA)-based binding matrix 102a and a protein-based binding matrix 102b.

More specifically, the composition of the hydrogel matrix may include a glycosaminoglycan such as, but not limited to, sodium hyaluronate (i.e., tyramine cross-linked sodium hyaluronate), heparin/heparin sulfate, chondroitin sulfate/dermatan sulfate, or keratan sulfate. The composition may also include a tyramine cross-linked polyamino acid, which can mimic proteins and be ideal for drug delivery. Polyamino acids can be used in the hydrogel matrix to create molecules such as, but not limited to, collagen, elastin, or synthetic polypeptides. In some embodiments, the composition may include tyramine cross-linked molecules with a carboxyl functional group, wherein the molecules are a biopolymer or a biocompatible polymer. Biopolymers used to create hydrogels may have tyramine substitution rates from 0.1% to 7.0%, although some formulations may use lower or higher substitution rates. Preferably, substitution rates of 1.0-5.0% are typical for this use.

There are various mechanisms by which cross-linking to create the binding matrix 102 may occur. However, in a preferred embodiment, an enzyme, such as horseradish peroxidase (HRP), is used in combination with a cross-linking agent to cross-link the liquid hydrogel matrix. For example, in one embodiment, hydrogen peroxide ($H_2O_2$) in combination with HRP may be used to induce cross-linking. In another example, various chemicals or light waves can be used to create free radicals in the hydrogel matrix that HRP then uses to cross-link the tyramine molecules. For example, ultraviolet (UV) light by itself or in combination with HRP may be used to induce cross-linking. In a further embodiment, titanium dioxide (TiO$_2$) may be added to UV and HRP and used as a catalyst to induce cross-linking. In yet another embodiment, gamma irradiation may be used with TiO$_2$ and HRP to induce cross-linking to create the binding matrix 102. In yet another embodiment, ionizing radiation used with HRP will induce cross-linking.

The composition of the binding matrix 102 may include ranges of concentrations of specific molecules. For example, the concentration of a THA in water may range from 0.0% to 20.0% and H$_2$O$_2$ may be diluted, with its concentration depending on the concentrations of HRP and THA. In some embodiments, water is the preferred buffer (although other buffers such as saline or phosphate are considered) because it creates high osmolality in the binding matrix 102, which then causes the binding matrix 102 to absorb fluid from the surrounding tissue. By absorbing additional fluid (i.e., water) from surrounding tissue, the process of drug elution out of the binding matrix 102 is slowed.

Tyramine Cross-Linked Biopolymer: Sterilization/Sanitation

In some embodiments, specific sterilization and sanitation measures may be taken to ensure the delivery system 100 does not cause further problems when injected or used on a patient. For example, the delivery system 100 may use aseptic preparation such as sterile filtration. Another method of sterilizing may include ethylene oxide sterilization (ETO), which can chemically sterilize the delivery system 100. Further methods that can be used are gamma irradiation and/or hydrogen peroxide plasma sterilization. Various preservatives may also be used to maintain sterile conditions.

Tyramine Cross-Linked Biopolymer: Physical Form

The binding matrix 102 comprised of a tyramine cross-linked biopolymer may come in a variety of physical forms. One such form may be a hydrogel, and the hydrogel may come in a spectrum of consistencies depending on how long the drug reservoirs 104 need to stay in tact and in the binding matrix 102. For example, a less dense, more liquid binding matrix 102 having a low concentration of a tyramine cross-linked biopolymer will dissolve faster resulting in faster rates of drug or target molecule delivery, whereas a denser, hard, tyramine cross-linked biopolymer particle will dissolve slower resulting in slower rates of drug or target molecule delivery.

Figure 8:
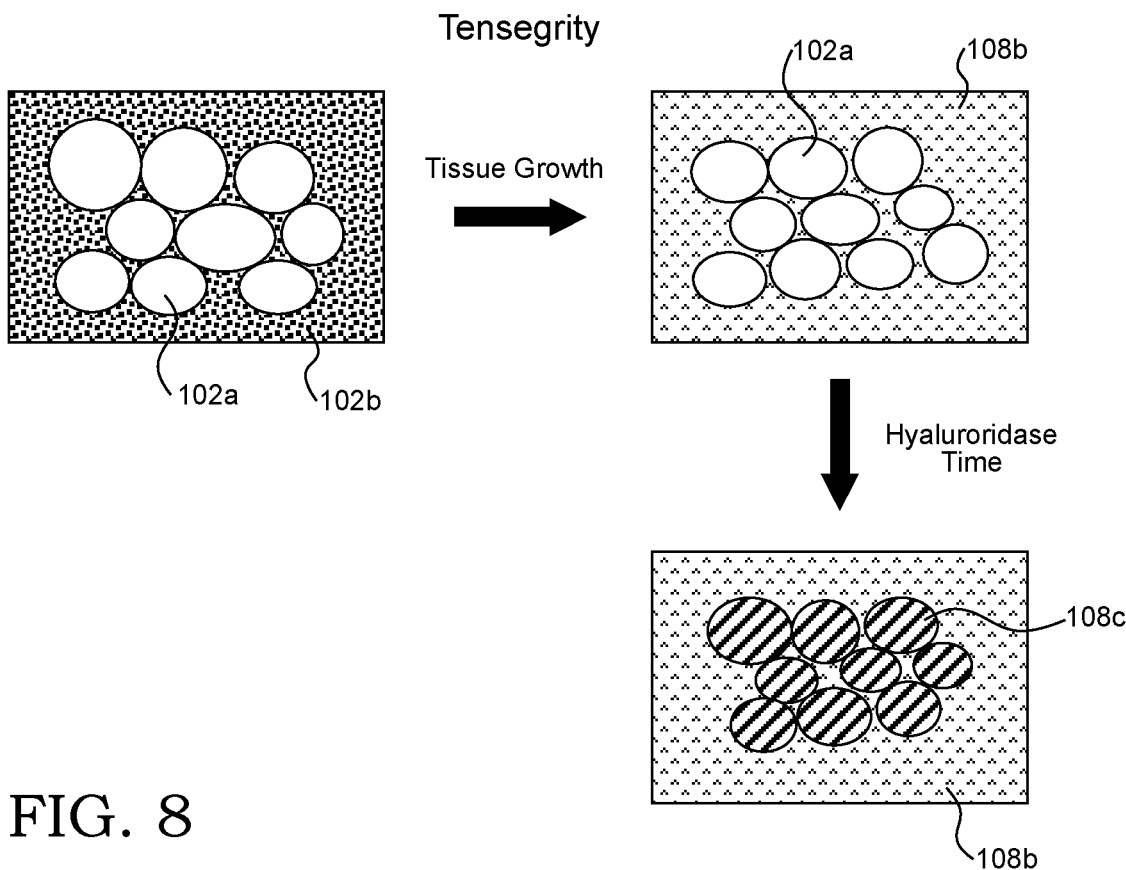
FIG. 8 illustrates tensegrity formed through the use of two variations of the disclosed delivery system.
Figure 9:
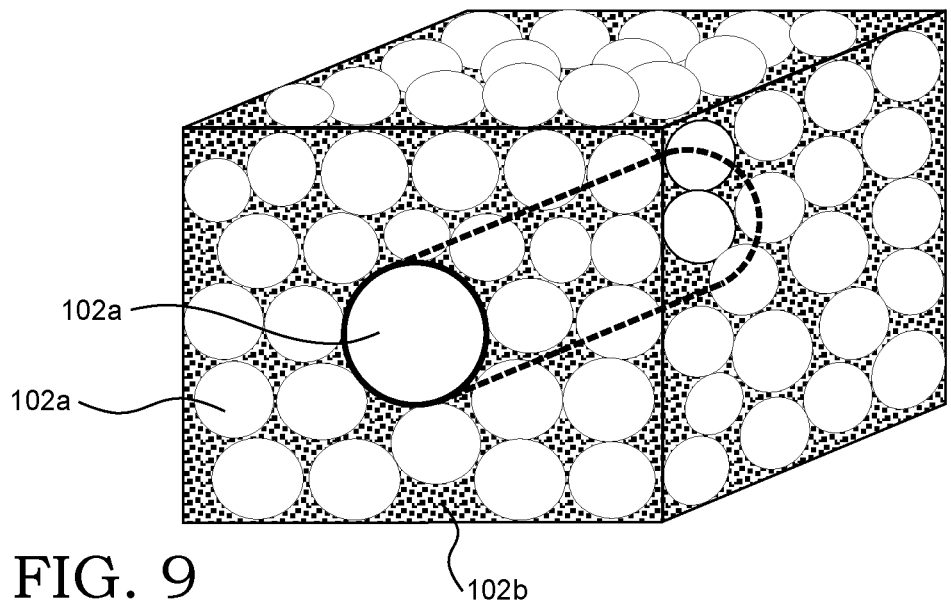
FIG. 9 illustrates nested geometries formed through the use of two variations of the disclosed delivery system.
Figure 10:
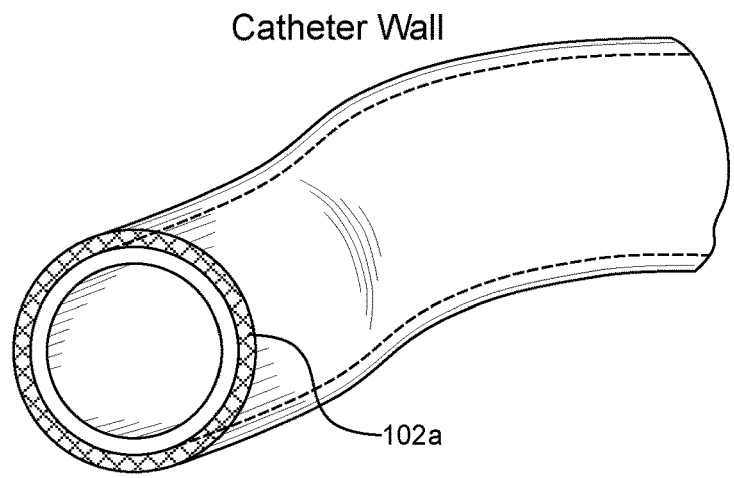
FIG. 10 illustrates a catheter wall coated with one embodiment of the disclosed delivery system.
Figure 11:
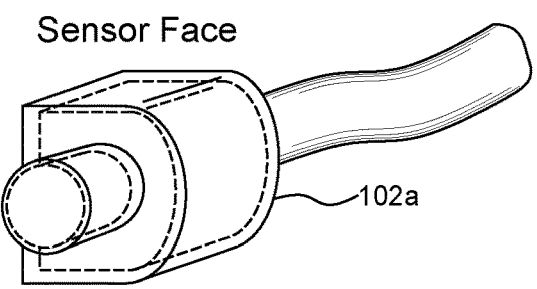
FIG. 11 illustrates a sensor face coated with one embodiment of the disclosed delivery system.
Figure 12:
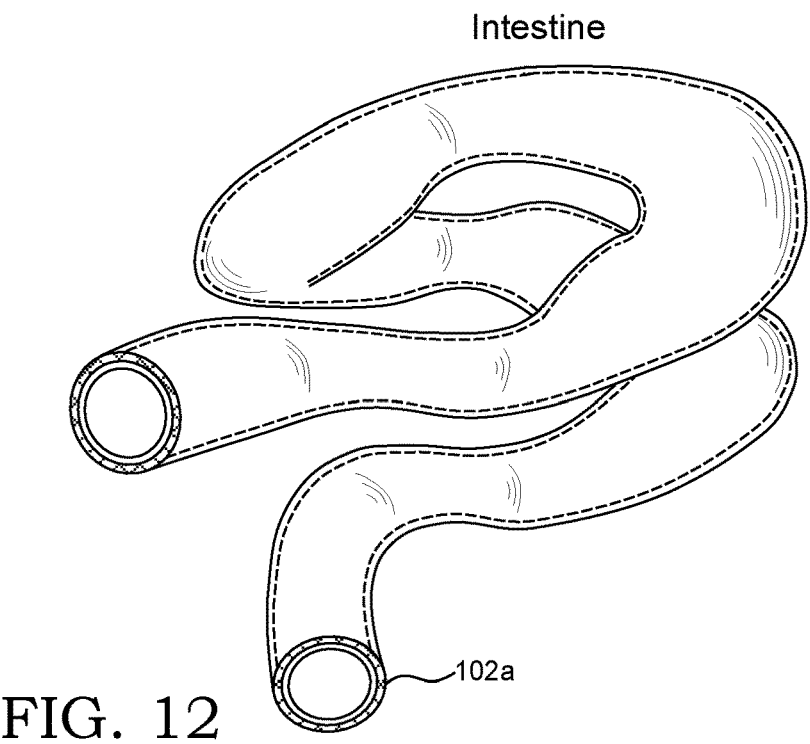
FIG. 12 illustrates a portion of an intestine coated with one embodiment of the disclosed delivery system.

In some embodiments, the physical form of the delivery system 100 may have bidirectional tensile strength and/or may be available to use in a multi-component reaction. In some embodiments, the physical form may be a coating, as illustrated in FIGS. 10-12, and/or may have tensegrity (for example, nested geometries), as illustrated in FIGS. 8-9. Tensegrity is useful in situations where a signaling or growth promoting molecule may need to be delivered. Other physical forms that the delivery system 100 may take include, but are not limited to, sheets, cords, woven or non-woven mesh (for example, woven tubes), dry powder (for example, mixed powders), or particles. The particles may come in a variety of sizes (for example, submicron to macro particles) and may have reproducible size distribution. They may also come in different densities. For example, dense particles may operate as a drug reservoir 104 and loose particles may operate as binders for nanoparticles.

Coating

Coatings are important for many medical device applications. For example, the delivery system 100 can be used to create a coating by using techniques such as, but not limited to, covalent bonding to a polymer surface, or by simply relying on mechanical adhesion to the surface of the device. Additionally, once attached to the medical device surface, the coating can be augmented by adding material and then cross-linking new layers to the base layer that is in contact with the medical device. Coatings can also occur on non-medical devices, such as gauze, to prevent bonding of new tissue 108b to the gauze.

Layers of different composition can also be created if desired such as, but not limited to, a basal layer of THA-based binding matrix 102a covered by a layer of collagen or protein-based binding matrix 102b. Similarly, a THA-based binding matrix 102a can be coated with an anticoagulant material (for example, warfarin or modified warfarin) that can cross-link to the THA-based binding matrix 102a.

One example of a specific use case is coating the THA-based binding matrix 102a on biological sensors. For example, THA-based binding matrix 102a can be coated on a glucose blood sensor via covalent bonding, as illustrated in FIG. 11. This coating could prevent fouling at the surface of the blood glucose sensor, which changes the rate of diffusion for what is being measured and, therefore, causes false readings. By preventing connective tissue (i.e., scar tissue) formation on the surface of the biological sensor, the THA-based binding matrix 102a can provide similar mass transport properties of surrounding tissues to ensure that measurements are not altered.

Tensegrity

In some embodiments, the disclosed delivery system 100 acts as a synthetic equivalent to natural made collagen structures and is, therefore, able to contribute to biological tensegrity, wherein the surrounding tissue 108a may migrate into the basal material and start forming new tissues 108b based on the tissue cell shape, size and spacing of the surrounding tissue 108a. Therefore, as a result, the basal material (i.e., the delivery system 100) can help regrow the tissue as it was before. For example, the disclosed technology could create artificial collagen or protein-based structures that mimic natural organs or tissues and allow stem cells and migrating endothelial cells to recreate the new organs or tissues 108b.

More specifically, one method of recreating new organs or tissues is to create a void by creating particles of mixed composition, as illustrated in FIG. 8. One set of particles could be a protein or collagen-based binding matrix 102b while the voids, or second set of particles, could be created from the THA-based binding matrix 102a. Using hyaluronidase after a stable cross-linked protein structure is formed can allow voids of preferred shape and size to form within the protein-hydrogel new tissue structure 108b. Cells that are placed within the structure 108b, such as generic stem cells or cells from surrounding tissue, could then be encouraged to form new tissues 108c as directed by the size and shape of the voids in the protein structure 108b (i.e., the cells will differentiate into proper tissue types). This process naturally takes place when a scab acts as the scaffold. However, it is not an ideal solution because scar tissues form. The use of the THA-based binding matrix 102a prevents formation of connective (i.e., scar) tissue.

Another option to recreate new organs or tissues is to print multiple shapes (for example, ovoids, spheres, cubes, etc.) to create a custom cellular scaffold. Alternatively, a collagen scaffold from living tissue could be used and could be coated with the protein-based binding matrix 102b to encourage cellular differentiation and, therefore, tissue growth 108b.

Nested geometries can add on to the tensegrity, as illustrated in FIG. 9, wherein a second, higher level of structure can be created to mimic blood vessels, tendons, connective tissue, etc. Structural elements created by or coated with THA-based binding matrix 102a can be added to hold the structure together during growth of new tissue 108b. This enables creation of microscopic/cellular level geometry as well as macro geometry or large voids or separations between tissue layers (for example, if THA-based binding matrix 102a is coated on each layer). More specifically, the vessels may connect naturally to surround the created vasculature and may provide nutrients and oxygen to the developing tissue 108b. Depending on the complexity of the new organ or tissue 108b being created, additional higher levels of organization can occur.

Sheets

Figure 5:
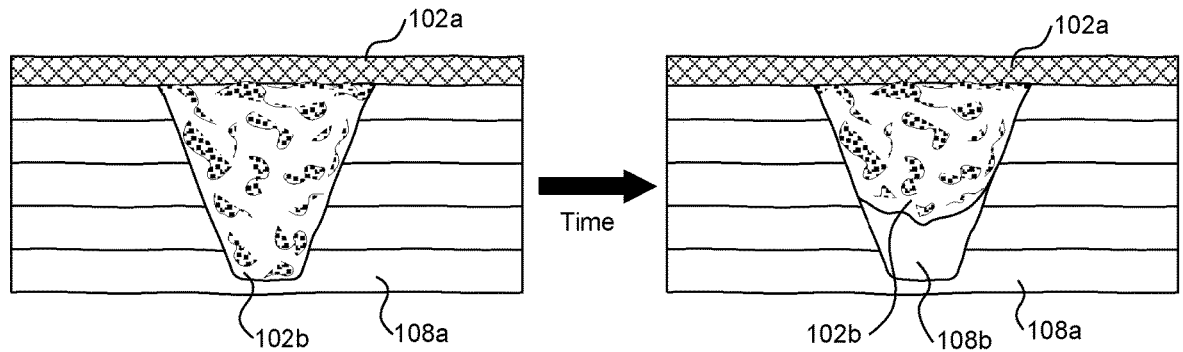
FIG. 5 illustrates two variations of the disclosed delivery system used to heal deep-penetrating wounds.
Figure 6:
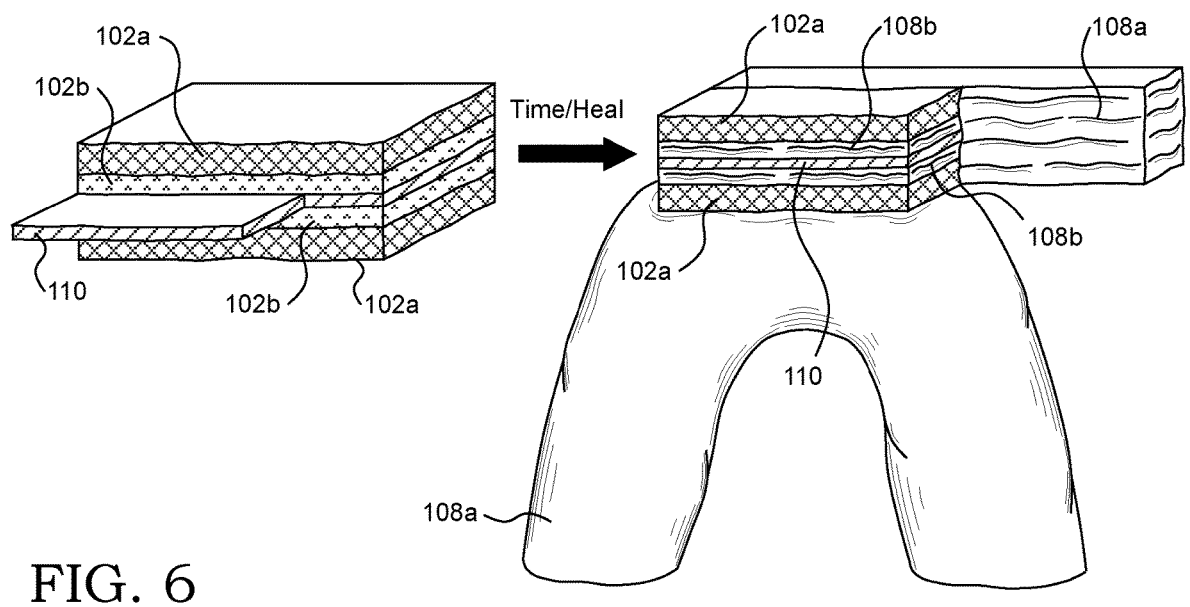
FIG. 6 illustrates one example of a tissue or hernia patch having two variations of the disclosed delivery system.
Figure 7:
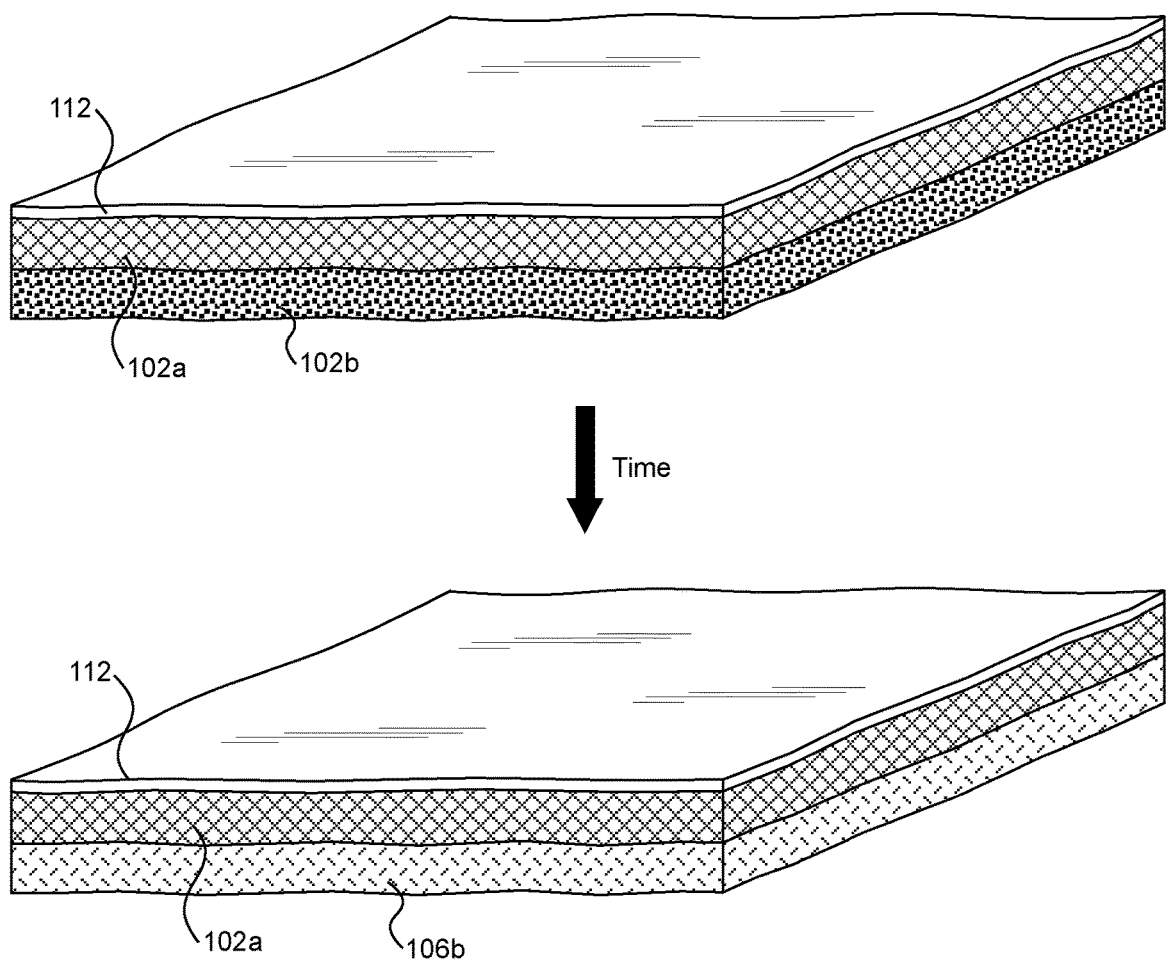
FIG. 7 illustrates artificial skin having two variations of the disclosed delivery system.

Generally, the hydrogel matrix may have a low tensile strength. However, in some embodiments, the binding matrix 102 may be a high concentration, protein-based binding matrix 102b that has a useful tensile strength. This type of binding matrix 102 could be in the form of a sheet that could be applied to tissue surfaces 108a, as illustrated in FIGS. 5-7. This hydrogel sheet delivery system 100 could, in some embodiments, protect the tissue surface 108a from desiccation or injury. In other embodiments, it could prevent tissue surfaces 108a from forming scar tissue or connective tissue after surgery.

While some previously known products may have a sheet of hydrogel, the sticky nature and difficulty of use prevent widespread use. In the disclosed case, a resorbable material could be used as the basal material to allow easy deployment into the body. Another benefit of using an embodiment of the disclosed delivery system 100 is that it can retain the benefit of the hyaluronan-based binding matrix 102a. More specifically, due to its hygroscopic nature, it can prevent connective tissue formation and desiccation.

A hydrogel sheet delivery system 100 can also be created to use as a base for growth of new tissue 108b. For example, FIG. 7 illustrates a case of skin replacement, wherein a non-resorbable polymer sheet 112, which can be a woven or nonwoven sheet, can be coated with a THA-based binding matrix 102a and a protein-based binding matrix 102b that is impregnated with dermal base tissue and can be applied to a traumatic wound surface 108a. The binding matrices 102a, 102b may also include drugs or medications 106 that help with pain relief, that promote healing, or that are growth promotion biofactors. The protein-based binding matrix 102b can encourage cells to migrate to the wound site 108a and create new skin 108b, while the THA-based binding matrix 102a, sandwiched between the polymer sheet 112 and the protein-based binding matrix 102b can prevent newly created tissue 108b from binding directly to the polymer sheet 112. The polymer sheet 112 can protect and seal the wound, preventing the binding matrices 102a, 102b from losing water and providing mechanical support. Alternatively, if necessary, a porous or membrane material can be used to allow an influx of oxygen to the wound surface 108a during healing. In another embodiment, the binding matrices 102a, 102b can be applied to the surface without the polymer layer 112.

Cords

As disclosed above, another physical form that the disclosed delivery system 100 can take is the form of cords, wherein the cords can be formed either as a single fiber or cord, or woven from several base fibers. Woven ropes of material may have a hollow core or solid kerns. In a preferred embodiment of the delivery system 100 in the form of cords, the cords can provide the tensile strength needed for holding surfaces stable relative to each other. More specifically, the delivery system 100 can be used to coat and fill gaps within the cord or rope of biopolymers.

Although there are likely to be applications where a cord or rope base would need to stay in the body long term (for example, stainless or titanium mesh in bone repair, arthroplasty, tendon repair, etc.), in nearly all applications it is desirable to build the cord support with resorbable materials. Resorbable materials include, but are not limited to, polyglycolic acid, polydioxanone, and polycaprolactone. Preferred polymers to use could contain glycolide, caprolactone, trimethylene carbonate, l-lactides, and p-dioxanones. However, silk, proteins, and other natural biopolymers may work as well. Xenographic and autographic tissues could also be acceptable for use in some of these applications.

Mesh

Mesh is an additional physical form that the disclosed delivery system 100 may take. A mesh base can be used to support the relatively fragile binding matrix 102 when the hydrogel's tensile strength is necessary to hold tissue edges stable relative to each other (i.e. when closing a gap, hole, or void in tissue). A mesh base can also act as mechanical support when large volumes of hydrogel are required to remain in place after placement.

In some embodiments, a mesh base may be in the form of a sheet, wherein the mesh or fabric sheets can come in woven and non-woven forms. Although there are likely to be applications where a mesh base would need to stay in place in the body long term (for example, stainless or titanium mesh in bone repair, arthroplasty, etc.), in nearly all applications it is desirable to build the mesh or fabric support with resorbable materials, which may be comprised of the materials as described above.

Mesh: Woven

One form of mesh sheet is a woven sheet. In some embodiments, the base material of woven fabrics and sheets may be formed into long threads, fibers, and/or strings, which may be woven together into sheets of usable size. Woven materials may have variable tensile strengths depending on the materials of construction and relative direction of fibers. Warp threads are interlacing threads that hold the weft thread in place. Fabric properties may depend on the material properties of the weft and warp threads as well as the packing density and size of threads.

One example of a woven sheet of hydrogel is a woven tube. Woven tubes can be incorporated into the walls of tube structures to provide mechanical strength to materials. In some cases, the woven supports could be layered to contain materials or tissue within the sheets.

Mesh: Nonwoven

A second form of mesh sheet is a nonwoven sheet. In some embodiments, nonwoven fabrics are created with a mixture of variable thread lengths, wherein the variable thread lengths are bonded together using heat, mechanical entanglement, or chemical bonding. In some embodiments, a nonwoven fabric may be bonded to a woven fabric when additional tensile strength is required for the material.

For example, FIG. 6 illustrates use of a hernia patch, wherein a high tensile biopolymer 110 may be covered on both sides by a protein-based binding matrix 102b that attracts macrophages and endothelial tissue for growth of new tissue 108b, which itself is surrounded by a THA-based binding matrix 102a. Macrophages can break down the protein-based binding matrix 102b material to enable neighboring cells to come in and do wound healing. In another embodiment, a strong resorbable woven fabric base may be covered on both sides by a nonwoven fabric that has a large contact area to which the hydrogel 102 can be mechanically bound. The advantage of this type of construction is that the base material can provide sufficient tensile strength to keep the hole closed. Additionally, the THA-based binding matrix 102a could prevent the body from forming scar tissue between the patch and surrounding original tissues 108a, and it could allow the body to resorb and create new tissue 108b around the base fabric, thereby creating new tissue 108b in the void with directional selectivity.

Tyramine Cross-Linked Biopolymer: Methods of Delivery

Syringe

The delivery system 100 may be delivered using a variety of methods. In one embodiment, a syringe may be used. For example, the syringe may be used in combination with a needle, a coater, a nozzle, a catheter, or oral dosage.

In an embodiment using a coater, the coater can create one to two-inch wide thin sheets of the delivery system 100 by expelling the delivery system 100 through a syringe in a plastic or metal applicator that expels the delivery system 100 through a die face in a sheet form. This is useful when trying to apply the delivery system 100 to a large tissue surface 108a in order to protect the target tissue 108a, or to create a high surface area from which to elute drugs, biologics, or target molecules 106 to the tissue 108a. Nozzles of various shapes and geometries can also be used to expel a larger volume of the delivery system 100 to or into a void or target tissue 108a.

In the case of a catheter, the tunability of the delivery system 100 may allow it to, in a liquid configuration, be extruded through a small diagnostic catheter. Alternatively, the individual components (the binding matrix 102, drug reservoirs 104 having drugs or target molecules 106, enzyme, and cross-linking agent) may be mixed just before entering the catheter so that the cross-linking reaction occurs within the body. This may be desirable when a large volume of material needs to be expelled from the catheter, as it allows for ease of delivery. Importantly, reaction rates can be modified in many ways (i.e. enzyme concentration) so that after delivery and a short manipulation setup time, the delivery system 100 can be sculpted into a desired form. Situations related to embolics, cardioplasty, mitral valves, and dermal fillers may benefit from a delayed set up time. Catheter-based applications, specifically, could include embolics or fillers for embolic wires.

Assist Devices

In some embodiments, a thick solution of the delivery system 100 may be needed as an application on or to the target tissue 108a. In these situations, assist devices may be used such as a ratcheting screw, a screw, or a trigger device.

A ratcheting screw is, in a preferred embodiment, a high pressure syringe and plunger configuration in which the plunger is threaded and delivers a series of set volumes, wherein the amount delivered is known due to a clicking noise that is created when a tab on the plunger impinges upon a second tab on the syringe body. The screw-like configuration can allow delivery of materials under high pressure that are not obtainable with standard syringes. One variation may be a device in which the pre-cross-linked binding matrix 102 can be contained in a first barrel, and the cross-linking agent, such as hydrogen peroxide, can be contained in a second barrel for delivery through a catheter or other small lumen.

A screw assist device is similar to the ratcheting screw assist device. However, the screw assist device has no audible notification of volume delivered. Therefore, it is best used when large final volumes that are required under high pressure are not required to be precisely accurate.

A trigger device may also assist with application of a thick solution of the delivery system 100. It is similar to a caulk gun, wherein it can, in response to a linear motion of a trigger pull, drive a plunger and expel the thick material from the syringe. This would be convenient for more precise control of flow.

Visualization

In addition to various methods of delivery, some embodiments of the delivery system 100 include the ability to visualize the delivery system 100 after it has been administered to a patient. These methods include, but are not limited to, contrast agents and solid pigments, such as radiopaque and color-based pigments. Visualization and location of compounds and implants can be a difficult, yet critical, activity for proper function and use of medical devices and delivery of pharmacologically active components. The delivery system 100 disclosed herein offers an opportunity to visualize placement of a medical device via fluoroscopy, direct visualization, ultrasonic, fluorescence, and combinations or variations of all the above.

Contrast agents can be used in applications where the binding matrix 102 and its contents are delivered via syringe, catheter, or other remote device to a location that cannot be directly observed but could be visualized under fluoroscopy by incorporating an iodine-based contrast agent within the delivery system 100. The contrast agent could be dissolved directly into the binding matrix 102, it could be contained within dense hydrogel particles carried within the binding matrix 102, or it could be contained within other drug reservoirs 104 that would retain the contrast for the duration of the procedure. Because the contrast would eventually elute out of the binding matrix 102 and particles or other reservoirs 104, ideally, this method would be used in applications where the contrast would only be needed for visualization for a short period of time. After the short period of time, the contrast agent would no longer be visible via fluoroscopy.

Solid pigments or particles, such as radiopaque (pigments and solid materials that are opaque to x-rays) and color, could be added to the binding matrix 102 for specific labeling purposes. A solid pigment, contrary to a contrast agent, will not elute from the delivery system 100 and would essentially be a permanent visualization of the delivery system 100 unless and until the body has absorbed the binding matrix 102, the drug reservoirs 104, and the drugs or target molecules 106. In some embodiments, the binding matrix 102 could be an anchoring site for living organisms such as xenografts or engineered single cell organisms. These living organisms can be designed to supplement or process metabolic compounds or to produce compounds that elicit a desired effect on the surrounding tissue 108a.

Examples of radiopaque materials include, but are not limited to, tantalum pentoxide (TaOx), titanium dioxide ($TiO_2$), Pt/Ir, iron-based materials, zirconium, I bases, halogenated polymers, and crystallized polymers. Further explanation of some of these is included below.

Tantalum pentoxide can be used as a radiopaque label for embolics and coatings for medical devices. It can allow a medical device to be visualized under fluoroscopy since the substance is radiopaque. The material is biocompatible and negligibly soluble in water. Tantalum particles can be added to the precursors of the binding matrix 102 and, once suspended in the formulation, cross-linked in place. The retention of the radiopaque particles allows the delivery system 100 to be visualized for as long as the binding matrix 102 is present.

Titanium dioxide particles can also be used in a similar manner by being suspended in the liquid, hydrogel formulation and cross-linked in place. A unique property of $TiO_2$ is its ability to form ozone in the presence of water and ultraviolet light. A unique way to form the binding matrix 102 is to illuminate a binding matrix 102 containing $TiO_2$ with UV radiation. The peroxide enzyme would utilize the ozone to form the tyramine-tyramine cross-links. The bright white color of $TiO_2$ could also be a method to directly visualize the delivery system 100.

Pt—Ir is commonly used as a marker band on catheters and medical devices to visualize advancing surfaces. It is biocompatible and insoluble in water. Similar to previously described methods, particles of Pt—Ir can be suspended in the liquid, binding matrix 102 and then cross-linked in place. The delivery system 100 would then be visible under fluoroscopy.

Iron-based materials could be added to the delivery system 100 to make it radiopaque and visible under fluoroscopy. Low concentrations of FE/magnetic particles could be suspended in the binding matrix 102 and used to mobilize the drug reservoirs 104 and move them throughout the body to reach a desired tissue location. This may be of particular interest in tissues like the eye, where manipulation of the delivery system 100 may help flatten and reposition a detached retina tissue surface to the back of the eye. Once the repair is made, the delivery system 100 can be removed via similar motility methods.

Zirconia is a radiopaque material usually used in dental implants. It has a similar color to tooth enamel, is biocompatible, and is negligibly soluble in water. Zirconia particles can be suspended as described above and used to mark the delivery system 100 location under fluoroscopy.

Instead of radiopaque pigments and solid materials, some embodiments of the delivery system 100 may use solid color pigments or materials to visualize delivery. Dyes of various colors could be loaded into the binding matrix 102 to help directly visualize the delivery system 100. The dyes could elute from the hydrogel binding matrix 102 and would be used in applications that have a short visualization time. Examples of dyes include UV-fluorescence, visible, and reactive color changing dyes.

The dityramine cross-link fluoresces under ultraviolet light. During placement of the delivery system 100 or prior to surgical closure, a UV source can illuminate the site and determine whether the delivery system 100 has been correctly placed. This would be especially helpful for determining whether the delivery system 100 has completely coated a tissue 108a or completely filled a void or interstitial space.

Tyramine Cross-Linked Biopolymer: Drug Delivery

As disclosed herein, there are a plurality of ways that the drugs, target molecules, or other biological agents 106 in the drug reservoirs 104 can be delivered from the delivery vehicle 100 to the targeted tissue or organ site 108a. Some examples include, but are not limited to, elution and a binding matrix/retention. The drugs, target molecules, or other biological agents 106 to be delivered can include, but are not limited to, macromolecules or small molecules.

Macromolecules

Example macromolecules include, but are not limited to, monoclonal antibodies, which are, generally, very useful alone or in combination for treatment of autoimmune diseases, oncology, and other specific applications. However, monoclonal antibodies are usually present in low concentration in formulations because, when in solution, they bind to each other, crystallize or precipitate, and fall out of solution. Therefore, to increase the concentration of monoclonal antibodies present in a formulation, the binding matrix 102, which can cross-link in place without damaging the monoclonal antibodies, will have a reduced amount of liquid compared to liquid solution due to its solid nature and can, therefore, reduce movement of the monoclonal antibodies. By forcing the monoclonal antibodies to diffuse through the dense drug reservoir 104 to find each other, the delivery system 100 reduces the ability of the monoclonal antibodies to come into contact with each other and effectively prevents their aggregation, which allows them to be present in formulations in higher concentrations.

There are many applications involving the elution of monoclonal antibodies from a delivery system 100 that would assist in long-term treatment of conditions and diseases, such as macular degeneration, especially when the antibodies target signaling molecules or cascade intermediates.

Small Molecules

Example small molecules include embodiments such as, but not limited to, non-steroidal anti-inflammatory drugs (NSAIDS), steroids, anti-seizure medication, antibiotics, antifungals, biologics, anti-psychotics, platelet rich plasma (PRP), albumin, gout medications, teriparatides (such as FORTEO®), denosumabs (such as Prolia®), albumin, erythropoietin, and oncological medications.

Small Molecules: NSAIDS

NSAIDS that could be used are naproxen, ibuprofen, celecoxib, acetaminophen, aspirin, dexibuprofen, diflunisal, salsalate, fenoprofen, ketoprofen, dexketoprofen, flurbiprofen, oxaprozin, loxaprofen, indomethacin, tolmetin, sulindac, etodolac, ketorolac, diclofenac, aceclofenac, piroxicam, meloxicam, tenoxicam, droxicam, lornoxicam, phenylbutazone, mefenamic acid, meclofenamic acid, flufenamic acid, tolfenamic acid, clonixin, and licofelone.

Generally, NSAIDs are delivered in a small molecule drug elution. The drug reservoirs 104 may have higher concentration of THA. For example, depending on drug reservoir concentration requirements, they may have concentrations that are at least greater than 10% and that are preferably 10-20%. NSAIDs can be combined with carrier molecules. Otherwise, they can be impeded by an influx of water and serum from surrounding tissue 108a. In one embodiment, ibuprofen may be mixed with acetaminophen and contained within a binding matrix 102 for direct placement within tissues 108a, for application as a topical gel, or for mechanically adherence to an application film (for example, a patch). In this example, acetaminophen can bind to plasma proteins, which can make the ibuprofen more effective.

Many of the NSAIDS disclosed herein can be used to treat migraine, osteoarthritis, kidney stones, rheumatoid arthritis, psoriatic arthritis, gout, ankylosing spondylitis, menstrual cramps, tendinitis, macular edema, and bursitis. They may be applied directly near the treatment tissue or organ site 108a (i.e. via injection or gel application during surgery) or as a topical patch near the tissue or organ site 108a. They may be used in combination with antibiotics, antifungals, selective steroids (if localized), anticoagulants (for example, to prevent thrombosis), monoclonal antibodies, opioids, and other compounds. In some embodiments, acetaminophen may be a complement to an NSAID, in that it can bind to plasma proteins thereby making the NSAID more effective. In a drug eluting delivery system 100, however, the dosage could approach eight to ten times the typical dosage of an NSAID due to the medication's slow elution out of the delivery system 100. This is convenient for individuals who have to frequently receive medication directly from medical professionals. Drug reservoirs 104 could use up to 20% THA concentration at up to 7% tyramine substitution. Preferable concentrations are 1.5% substitution at 15-20% concentration. The binding matrix 102, which holds the drug reservoirs 104 in place, could use up to 1.5% substitution with concentrations adjusted to account for desired application consistency (i.e., a liquid-like form will have a lower concentration while a jelly-like form will have a higher concentration).

Naproxen is one example of an NSAID. Typical dosages of naproxen may range from 125 mg to 750 mg for a single administration. In the disclosed delivery system 100, however, the dosage could approach up to eight times this amount due to its slow elution.

Ibuprofen is another example of an NSAID. Typical dosages of ibuprofen may range from 200 mg to 800 mg for a single administration. In the disclosed delivery system 100, however, the dosage could approach eight to ten times this amount due to its slow elution.

Celecoxib is yet another example of an NSAID. Typical dosages of celecoxib may range from 100 mg to 400 mg for a single administration. In the disclosed delivery system 100, however, the dosage could approach eight to ten times this amount due to its slow elution.

Acetaminophen is another example of an NSAID. Typical dosages of acetaminophen range from 500 mg to 1000 mg for a single administration. In the disclosed delivery system 100, however, the dosage could approach eight to ten times this amount due to its slow elution.

Aspirin is a further example of an NSAID. Typical dosages of aspirin may range from 81 mg to 1 g for a single administration. In the disclosed delivery system 100, however, the dosage could approach eight to ten times this amount due to its slow elution.

Dexibuprofen is an additional example of an NSAID. Typical dosage of dexibuprofen is 500 mg to 1000 mg for a single administration. In the disclosed delivery system 100, however, the dosage could approach eight to ten times this amount due to its slow elution.

Other examples of NSAIDS wherein the dosage can be eight to ten times greater in the disclosed delivery system 100 compared to a typical administration include diflunisal, salsalate, fenoprofen, ketoprofen, dexketoprofen, flurbiprofen, oxaprozin, loxaprofen, indomethacin, tolmetin, sulindac, etodolac, ketorolac, diclofenac, aceclofenac, piroxicam, meloxicam, tenoxicam, droxicam, lornoxicam, phenylbutazone, mefenamic acid, meclofenamic acid, flufenamic acid, tolfenamic acid, clonixin, and licofelone.

Small Molecules: Steroids

Steroids that could be used are progestogens (such as progesterone), corticosteroids, androgens (such as testosterone), estrogens, dexamethasone, moxifloxacin, interferon beta-1b, and glatiramer acetate.

Progesterone is one example of a steroid, and can be administered as a single bolus injection or topically applied as a gel or in a patch form. Progesterone can be used for amenorrhea, uterine bleeding, hyperplasia, progesterone insufficiency, premature labor, seizures, and premenopausal symptoms.

Various corticosteroids that could be used include alclometasone dipropionate, amcinonide, beclomethasone dipropionate, budesonide, betamethasone, betamethasone dipropionate, betamethasone valerate, cobetasol propionate, clobetasone butyrate, desonide, desoximethasone, dexamethasone, diflorasone diacetate, flunisolide, fluocinonide, fluocinolone acetonide, fluocortolone, fluticasone furoate, fluticasone propionate, mometasone furoate, ciclesonide, cortisone acetate, halcinonide, halobetasol propionate, halometasone, hydrocortisone aceponate, hydrocortisone acetate, hydrocortisone buteprate, hydrocortisone butyrate, hydrocortisone valerate, hydrocortisone, methylprednisolone, prednisone, prednicarbate, tixocortol pivalate, triamcinolone, and triamcinolone acetonide.

Alclometasone dipropionate is a corticosteroid that can be applied as a topical gel, as a patch, or in another delivery form. In a preferred embodiment, however, topical application in gel or liquid form is desired. Concentrations may vary depending on steroid strength. For example, if administration of the delivery system 100 is via patch or single delivery, alclometasone dipropionate may be administered with up to ten times its typical dosage, depending on the application site, the physical form of the delivery system 100 and reservoir drug concentration. Typical binding matrices 102 containing alclometasone dipropionate would be comprised of up to 7% tyramine substitution at up to 20% THA concentration. The binding matrix 102 may, in a preferred embodiment, have less than 1.5% tyramine substitution and less than 5% THA concentration.

Several other corticosteroids such as, but not limited to, amcinonide, beclomethasone dipropionate, betamethasone dipropionate, cobetasol propionate, clobetasone butyrate, desonide, desoximethasone, diflorasone diacetate, flunisolide, fluocinonide, fluocinolone acetonide, mometasone furoate, halcinonide, halobetasol propionate, halometasone, hydrocortisone aceponate, hydrocortisone acetate, hydrocortisone buteprate, hydrocortisone butyrate, hydrocortisone valerate, hydrocortisone, prednicarbate, tixocortol pivalate, and triamcinolone, can also be applied as a topical gel, as a patch, or in another delivery form. In preferred embodiments, however, topical application in gel or liquid form for these drugs is desired. Concentrations may vary depending on steroid strength. For example, if administration of the delivery system 100 is via patch or single delivery, the above-listed drugs may be administered with up to ten times their typical dosages, depending on the application site, the physical form of the delivery system 100 and reservoir drug concentration. Typical binding matrices 102 containing the above-listed drugs would be comprised of up to 7% tyramine substitution at up to 20% THA concentration. The binding matrix 102 may, in a preferred embodiment, have less than 1.5% tyramine substitution and less than 5% THA concentration.

Budesonide is a corticosteroid that can be used as an inhaler. With sustained release, the inhaled form of the disclosed technology could be superior due to a less frequent need for an inhaler dose. Drug reservoir particles 104 would likely be very small (<1 micron) to have the proper size and ability to contact lung tissue 108a and release the steroid. Tyramine substitution may be less than 1% to ensure complete absorption by the body, and the drug reservoir 104 would likely be solid in form so a propellant could carry it. Budesonide can also be used to treat rhinitis and nasal polyps. To treat these, the physical form may be a thin liquid. For example, it could be the THA-based binding matrix 102a, wherein the binding matrix 102a has less than 1% tyramine substitution and less than 1% THA concentration. The drug reservoirs 104 could be 1.5% tyramine substitution or less and up to 20% THA concentration. To treat inflammatory bowel disease, Crohn's disease, and ulcerative colitis using budesonide, the delivery system 100 may be applied as a suppository. The drug reservoirs 104 could be 5.5%-7% tyramine substitution and up to 20% THA concentration, while the binding matrix 102 could be 1.5% tyramine substitution and up to 10% THA concentration. The suppository can be a thick gel or can have a solid, gelatin-like consistency.

Betamethasone is a corticosteroid that may be injected or applied as a cream and can be used to treat skin disorders, allergic conditions such as asthma, preterm labor for neonatal lung development, Crohn's disease, inflammatory bowel disease ("IBD"), and adrenal insufficiency. One restriction for betamethasone's use in the delivery system 100 is that, in an injected form, it should be able to be injected with a reasonably-sized needle. In some embodiments, the drug reservoirs 104 are dense hydrogel particles that may consist of up to 1.5% tyramine substitution and up to 20% THA concentration, while the binding matrix 102 could be up to 1.5% tyramine substitution with up to 1% THA concentration. While binding matrices 102 can consist of up to 7% tyramine substitution and up to 20% THA concentration, a preferred embodiment for betamethasone would be up to 1.5% tyramine substitution and less than 5% THA concentration.

Betamethasone valerate is a corticosteroid that can be applied as a topical gel, as a patch, or in another delivery form and can be used to treat a large number of diseases and conditions such as, but not limited to, rheumatoid arthritis, systemic lupus, dermatitis, psoriasis, asthma, preterm labor lung development, Crohn's disease, IBD, and types of blood cancers. Concentrations may vary depending on steroid strength. For example, if administration of the delivery system 100 is via patch or single delivery, betamethasone valerate may be administered with up to ten times its typical dosage, depending on the application site, the physical form of the delivery system 100 and reservoir drug concentration. Typical binding matrices 102 containing betamethasone valerate would be comprised of up to 7% tyramine substitution at up to 20% THA concentration. The binding matrix 102 may, in a preferred embodiment, have less than 1.5% tyramine substitution and less than 5% THA concentration.

Dexamethasone is a corticosteroid with anti-inflammatory and immunosuppressant properties that may be injected or applied as a cream and can be used to treat a large number of diseases and conditions such as, but not limited to, rheumatoid arthritis, systemic lupus, dermatitis, psoriasis, asthma, preterm labor lung development, Crohn's disease, IBD, and types of blood cancers. It can also be used as a complement to pain medication in viscosupplementation applications. One restriction for dexamethasone's use in the delivery system 100 is that, in an injected form, it should be able to be injected with a reasonably-sized needle. In some embodiments, the drug reservoirs 104 are dense hydrogel particles that may consist of up to 1.5% tyramine substitution and up to 20% THA concentration, while the binding matrix 102 could be up to 1.5% tyramine substitution with up to 1% THA concentration. While binding matrices 102 can consist of up to 7% tyramine substitution and up to 20% THA concentration, a preferred embodiment for betamethasone would be up to 1.5% tyramine substitution and less than 5% THA concentration.

Fluocortolone is a corticosteroid that may be applied as a gel or suppository and can be used to treat hemmorhoids. In some embodiments, the drug reservoirs 104 could be 5.5%-7% tyramine substitution and up to 20% THA concentration, while the binding matrix 102 could be 1.5% tyramine substitution and up to 10% THA concentration. The suppository can be a thick gel or can have a solid, gelatin-like consistency.

Fluticasone furoate, fluticasone propionate, ciclesonide, and triamcinolone acetonide are corticosteroids that may be applied as a nasal gel but, in a preferred embodiment, are applied as a mist to the mucosal membranes for treatment of rhinitis, nasal polyps, and asthma. Ideally, the drug reservoirs 104 would be very fine and would be suspended in a liquid carrier solution so a propellant can carry the solid particle form. In some embodiments, an inhaler may be used, although the drug reservoir particles 104 would likely be very small (<1 micron) to have the proper size and ability to contact lung tissue 108a and release the steroid. In some embodiments, the drug reservoirs 104 could be up to 1.5% tyramine substitution (1% in the case of ciclesonide and triamcinolone acetonide) to ensure complete absorption by the body and 10-20% THA concentration. While the osmolality of the drug reservoirs 104 are preferred to be neutral, variations may be made to control the elution rate of the fluticasone furoate and/or fluticasone propionate.

Cortisone acetate is a corticosteroid that can be used to treat pain and swelling due to inflammation and joint, tendon, or bursa trauma. Additionally, cortisone acetate is an ideal candidate for combining with NSAIDs, cortisone, and viscosupplement components. For example, acetaminophen and cortisone acetate could combine with ibuprofen in a viscosupplementation hydrogel. In some embodiments, the drug reservoirs 104 are dense hydrogel particles that may consist of up to 1.5% tyramine substitution and up to 20% THA concentration, while the binding matrix 102 could be 1.5-7% tyramine substitution with up to 1% THA concentration. While binding matrices 102 can consist of up to 7% tyramine substitution and up to 20% THA concentration, a preferred embodiment for cortisone acetate would be up to 1.5% tyramine substitution and less than 5% THA concentration.

Methylprednisolone, a corticosteroid that may be injected or applied as a cream, and prednisone, a corticosteroid with immunosuppressant properties that may be administered orally or injected, can be used to treat skin disorders, allergic conditions, Crohn's disease, IBD, and adrenal insufficiency. One restriction for methylprednisolone and prednisone's use in the delivery system 100 is that, in an injected form, they should be able to be injected with a reasonably-sized needle. In some embodiments, the drug reservoirs 104 are dense hydrogel particles that may consist of up to 1.5% tyramine substitution and up to 20% THA concentration, while the binding matrix 102 could be up to 1.5% tyramine substitution with up to 1% THA concentration. A preferred embodiment for methylprednisolone and prednisone would be up to 1.5% tyramine substitution and less than 5% THA concentration.

Testosterone is an androgen steroid that can be used for testosterone insufficiency and can be applied as a topical gel, as a patch, or in another delivery form (such as by injection for long-term elution that is superior to elution through skin via a patch or gel). In preferred embodiments, however, topical application of the delivery system 100 in gel or liquid form for these drugs is desired. Concentrations may vary depending on steroid strength. For example, if administration of the delivery system 100 is via patch or single delivery, testosterone may be administered with up to ten times its typical dosages, depending on the application site, the physical form of the delivery system 100 and reservoir drug concentration. Typical binding matrices 102 containing testosterone would be comprised of up to 7% tyramine substitution at up to 20% THA concentration. The binding matrix 102 may, in a preferred embodiment, have less than 1.5% tyramine substitution and less than 5% THA concentration.

Testosterone can also be administered to transgender patients and used in oncology to treat prostrate cancer. High doses of testosterone appear to kill prostrate cancer cells and injected bolus near the cancer can deliver a locally high dose for longer period of time (compared to situations where it is provided systemically) to ensure cancer cells are exposed to high testosterone dose. One potential danger is that low to moderate levels of testosterone may promote prostrate cancer growth. Therefore, if the testosterone dose is not sufficiently high, it could be harmful instead of helpful. As with the corticosteroids, one restriction for testosterone's use in the delivery system 100 is that, in an injected form, it should be able to be injected with a reasonably-sized needle. In some embodiments, the drug reservoirs 104 are dense hydrogel particles that may consist of up to 1.5% tyramine substitution and up to 20% THA concentration, while the binding matrix 102 could be up to 1.5% tyramine substitution with up to 1% THA concentration. Typical binding matrices 102 containing testosterone would be comprised of up to 7% tyramine substitution at up to 20% THA concentration. The binding matrix 102 may, in a preferred embodiment, have less than 1.5% tyramine substitution and less than 5% THA concentration.

Estrogen is a steroid that may be injected or applied as a topical gel, as a patch, or in another delivery form and can be used to treat estrogen insufficiency for menopausal women or transgender patients. One restriction for estrogen's use in the delivery system 100 is that, in an injected form, it should be able to be injected with a reasonably-sized needle. In some embodiments, the drug reservoirs 104 are dense hydrogel particles that may consist of up to 1.5% tyramine substitution and up to 20% THA concentration, while the binding matrix 102 could be up to 1.5% tyramine substitution with up to 1% THA concentration. Typical binding matrices 102 containing testosterone would be comprised of up to 7% tyramine substitution at up to 20% THA concentration. The binding matrix 102 may, in a preferred embodiment, have less than 1.5% tyramine substitution and less than 5% THA concentration.

In the topical or patch form of the delivery system 100, concentrations may vary depending on steroid strength. For example, if administration of the delivery system 100 is via patch or single delivery, estrogen may be administered with up to ten times its typical dosages, depending on the application site, the physical form of the delivery system 100 and reservoir drug concentration. Typical binding matrices 102 containing estrogen would be comprised of up to 7% tyramine substitution at up to 20% THA concentration. The binding matrix 102 may, in a preferred embodiment, have less than 1.5% tyramine substitution and less than 5% THA concentration.

Small Molecules: Antibiotics

Various antibiotics that can be used in the disclosed delivery system 100 are avalox (such as moxifloxacin), beta-lactams (such as penicillin derivatives and cephalosporins), macrolides, fluoroquinolones, tetracycline, chlortetracycline, oxytetracycline, demeclocycline, lymecycline, meclocycline, methacycline, minocycline, rolitetracycline, doxycycline, tigecycline, and aminoglycosides.

Small Molecules: Biologics

In some embodiments, biologics such as, but not limited to, copaxone (an immunomodulator) and betaseron (an immunosuppressant) may be administered via injection (for example, subcutaneously) and can be used to treat multiple sclerosis. By using the disclosed delivery system 100 to deliver the biologics, a higher concentration can be used, which results in less frequent injections. One restriction for biologics' use in the disclosed delivery system 100 is that, in an injected form, it should be able to be injected with a reasonably-sized needle. In some embodiments, the drug reservoirs 104 are dense hydrogel particles that may consist of up to 1.5% tyramine substitution and up to 20% THA concentration, while the binding matrix 102 could be up to 1.5% tyramine substitution with up to 1% THA concentration.

Small Molecules: Other

Other small molecules that could be included in the disclosed delivery system 100 could treat conditions and diseases such as seizures, psychosis, autoimmune diseases like rheumatoid arthritis and multiple sclerosis, gout, liver failure, anemia, and cancer. NSAIDS and gold could be used to help with rheumatoid arthritis. Teriparatide, denosumab, and albumin could be used for liver failure. Erythropoietin (EPO) could be used for anemia and cancer.

Aside from injection, and as briefly mentioned above, the delivery system 100 can be delivered and used for a variety of other applications such as, but not limited to, adhesion prevention, coagulation, tissue patch, tissue augmentation, drug delivery, orthopedic, coatings, plugs, and tissue engineering.

Tyramine Cross-Linked Biopolymer: Adhesion Prevention

Many invasive medical procedures and surgeries damage the inter tissues 108a during activities such as manipulation, cutting, sewing and drying that may occur during the procedure. Post surgery, the delivery system 100 can be applied in sheets or it can be injected as a mass that coats and sticks to affected tissue surfaces 108a, thereby preventing adhesion. Hyaluronan is a natural barrier in the body and keeps tissues 108a from scarring. One benefit of the disclosed delivery system 100 is that it enables the damaged tissue sites 108a to remain coated in the hyaluronan long enough for the unintended trauma to heal without forming scarring bridges of connective tissue between neighboring tissue surfaces 108a.

In some embodiments, the delivery system 100 having a THA-based binding matrix 102a is thick enough to coat and stick to tissue surfaces 108a, but thin enough to be applied through a syringe, application tube or bottle, or a special sheet applicator. Similar to other medical applications, other drugs or molecules 106 can be added to supplement healing and protect the effected tissues 108a. Various examples include, but are not limited to the following: (a) NSAIDS can be added to reduce swelling and treat pain, (b) antibiotics and antifungals can be added to protect the wound site 108a from infection, (c) strong analgesics can be added that will elute out of the hydrogel binding matrix 102 over time and treat localized pain, and (d) growth factors and promoters can be added that elute out over a week or longer and promote faster healing.

Tyramine Cross-Linked Biopolymer: Coagulation

Hemorrhaging from a traumatic wound, diffuse abrasion, or cuts and contusions on patients taking anticoagulants can quickly become life threatening if not stopped. The disclosed delivery system 100, in some embodiments, provides several options for promoting coagulation at the wound site 108a such as, but not limited to, dehydration, use of fibrin, use of specific osmolality, use of vasoconstrictors, or any combination of the above.

Coagulation: Dehydration

Figure 4:
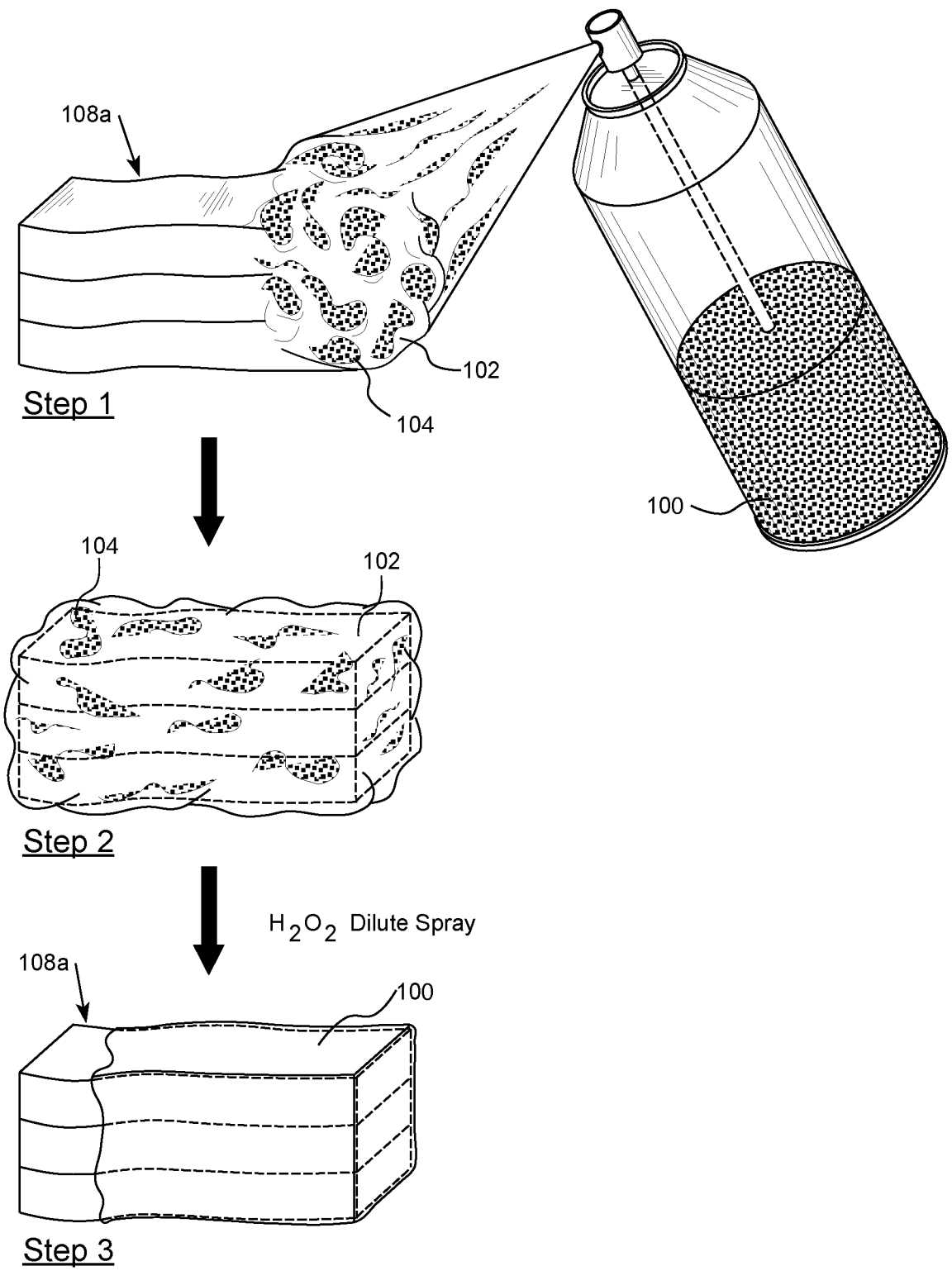
FIG. 4 illustrates a dry lyophilized binding matrix with drug reservoirs that is applied to a traumatic wound surface then cross-linked.

Absorbing and dehydrating the plasma component of blood promotes coagulation at the wound or trauma site 108a. Therefore, in one embodiment, a user can apply a delivery system 100 comprised of loose, powdered THA-based binding matrix 102a having drug reservoirs 104 to the affected tissue 108a that is bleeding and/or weeping, and allow it to absorb the plasma. In another embodiment, a user can apply the powder as a dry lyophilized gel powder from a dry powder aerosol delivery system having a propellant, as illustrated in FIG. 4, wherein a canister of dry lyophilized gel powder is pushed out and applied as a dry powder of the wound surface. FIG. 4 illustrates various tissues (for example, the epidermis, basal dermal layer, fat tissue, muscle layer) that are exposed due to trauma and are, therefore, benefiting from the disclosed delivery system 100. The powder could quickly stick to the blood or tissue surfaces 108a that are bleeding or weeping, absorb quickly, and cause coagulation. In some embodiments, the powder form of the binding matrix 102 can be pre-cross-linked when applied. In another embodiment, once the exudate is absorbed, a solution or mist of $H_2O_2$ can be applied to the THA-based binding matrix 102a causing it to cross-link the THA-based binding matrix 102a. The delivery system 100 can act as a physical barrier and as a tamponade.

Coagulation: Fibrin

In some embodiments, coagulation promoters, such as fibrin, can be added to the binding matrix 102 and cross-linked in place so that the fibrin remains active. The delivery system 100 having the cross-linked binding matrix 100 with fibrin can then be dispensed on a wound surface 108a as a sheet or series of sheets. In some embodiments, it can be injected in the center of a contusion to promote coagulation from the bleeding tissue.

Coagulation: Osmotic

Another way the delivery system 100 can promote coagulation is by using low substitution THA in high concentrations to create binding matrices 102 of high osmolality. The binding matrix 102 by itself has high enough osmolality to absorb water from surrounding tissues, collapsing bleeding capillaries, and small diameter vessels. However, adding a high loading of salts can further increase the osmolality. This application could also be used to collapse spider veins (arteries) in cosmetic applications.

Coagulation: Vasoconstrictors

In some embodiments, vasoconstrictors such as epinephrine and strong stimulants can be added to the binding matrix 102, cross-linked in place, and the final product can be applied to the wound site 108a or injected into a contusion. When used in combination with the binding matrix 102, vasoconstrictors can promote slowing of blood flow and escape from the vascular system while the binding matrix 102 can promote dehydration and coagulation of blood.

Coagulation: Combination Device

All of the above-described methods that promote coagulation may be used in any combination. They can create vasoconstriction in the capillaries and small vessels near the bleeding site while the binding matrix 102 and coagulation promoters cause the blood to coagulate and seal the wound surface 108a. Various supplemental components 106 may also be added to protect the site until additional medical treatment can be made such as, but not limited to, antibiotics, antifungals, analgesics, etc. In some embodiments, the delivery system 100 can form a protective physical barrier once it has covered the wound surface 108a and can operate like a natural scab.

Tyramine Cross-Linked Biopolymer: Tissue Patch

In addition to adhesion prevention and stimulating coagulation, the disclosed delivery system 100 may be used as a tissue patch to treat various disease states, as illustrated in FIG. 6 and described above. Polymeric tissue patches, netting, and hammocks consisting of Teflon, polypropylene, and polyethylene can cause the body to form scar tissue around an implant that can cause pain and may erode surrounding tissues, thereby compounding or making the tissue gap or hole worse. In one embodiment of the disclosed delivery system 100, the delivery system 100 may operate as a tissue patch that supports the surrounding tissue 108a, it may close holes and gaps, and/or it may maintain that closure long enough to allow the tissue to heal together. It can then absorb back into the body, thereby eliminating the need for its removal. The binding matrix 102 can also be loaded directly or indirectly (i.e., using drug reservoirs) with growth promoters, analgesics, collagen particles, or partially formulated from a collagen backbone so that supportive connective tissue can be formed over the gap or hole.

The delivery system 100, in its tissue patch form, may be used to heal wounds, offer mechanical support, or used for packing. The delivery system 100 can be formulated to include collagen particles or created by directly using small molecular weight collagen. The delivery system 100 can be combined with other tensile strong materials or other hydrogels to create a protective sheet. Similar to other applications, the binding matrix 102 can be loaded with drugs or target molecules 106 such as antibiotics, antifungals, analgesics, steroids, NSAIDS, etc. to treat symptoms of injury or traumatic wound.

In some embodiments, prior to placement and cross-linking, the binding matrix 102 can be seeded with red blood cells or white blood cells. In other embodiments, the binding matrix 102 can be seeded with red or white blood cells after cross-linking and after placement of the delivery system 100 by directly injecting the red or white blood cells into the binding matrix 102. In addition to red or white blood cells, the binding matrix 102 can be seeded, before or after placement or cross-linking, with plasma components, such as PRP. Once in place, the macrophages can attract fibroblasts, stem cells, and migrating tissue cells into the delivery system 100. Depending on the wound type and location, the delivery system 100 may have the best effect if applied in thin layers at regular time intervals. Serious, deep-penetrating wounds may respond best if the binding matrix 102, such as the protein-based binding matrix 102a, is applied as a single large bolus, as illustrated in FIG. 5.

More specifically, deep-penetrating wounds likely require new tissue growth 108b, which the disclosed binding matrix 102 is uniquely formulated to address. For example, as illustrated in FIG. 5, a protein-based binding matrix 102b can be applied at the wound site on or to the damaged tissues 102a, and a THA-based binding matrix 102a can be applied on top of the tissue 108a as a protective coat. Over time, the protein-based binding matrix 102b attracts macrophages and endothelial tissue for growth of new tissue 108b. Macrophages can break down the protein-based binding matrix 102b material and attracting epithelial or other neighboring cells into the binding matrix 102 to form new tissue 108b. The THA-based binding matrix 102a operates to protect the wound site and prevent scar tissue formation.

In addition to wound-healing, the disclosed delivery system 100 can supply mechanical support, can take the form of a hernia patch, can be used to help repair skin and muscles, can help repair or create new blood vessels, and can be used for packing.

Tyramine Cross-Linked Biopolymer: Tissue Augmentation

Another use of the disclosed delivery system 100 includes use for tissue augmentation. For example, the delivery system 100 can be used as dermal filler, for urology purposes (for example, for urinary or fecal incontinence), as a vitreal replacement, for myocardium tissues (for example, the mitral or aortic valve), for esophagus tissues, for gastrointestinal purposes (for example, gastric bypass), for vocal fold medicalization, for muscle fascia, as a void filler (for example, as an organ replacement), or as a heal pad (for example, for diabetics).

In regard to its use as dermal filler, the delivery system 100 can be created to be dense enough with sufficient duration to act as dermal filler. The sodium hyaluronate form can act as a filler to plump and expand dermal tissues so that they stretch the surface and remove folds and deep wrinkles. Additional components can be added to the hydrogel formulation to prolong the duration of the filler in the dermal tissue such as, but not limited to, collagen powder and/or fibers. These additional components can promote the formation of new tissue 108b by promoting migration of macrophages into the binding matrix 102 and attracting epithelial cells into the binding matrix 102 to form new dermal tissue 108b.

Tyramine Cross-Linked Biopolymer: Drug Delivery

In some embodiments, as described above, the delivery system can be used as a drug delivery vehicle. For example it can include drugs or target molecules 106 and, therefore, aid in wound healing, pain, oncology, and ophthalmology. It can include small molecule drugs, and it can act as a metabolic reservoir, a steroidal reservoir, or a dermal patch. The binding matrix 102 can be optically clear, have an optimal density for various tasks, and it can be absorbed, which would result in no need for post-treatment removal of the delivery system 100.

Tyramine Cross-Linked Biopolymer: Orthopedic

In some embodiments, the delivery system 100 can have use as an orthopedic tool. For example, it can aid with viscosupplementation, artificial cartilage, bone paste or cement, growth plate repair, tendon repair, and fasciitis. In regard to its use in viscosupplementation, the binding matrix 102 can be used to help supplement the synovial fluid, which is naturally comprised of 3-4 mg/mL hyaluronan and is a natural lubricant found in the bursae and tendon sheaths. As older joints and tissue fail to produce sufficient synovial fluid, they allow cartilage and, in severely damaged joints, bone to contact adjoining surfaces and create pain. Therefore, the binding matrix 102 can supplement the synovial fluid and enable the joint to heal enough to minimize pain. Because hyaluronan is usually recycled fairly quickly in the body, some embodiments of the disclosed invention may use an artificial hyaluronan solution that contains cross-linked hyaluronan that is resistant to enzymatic degradation. In other embodiments of the delivery system 100, a highly substituted and cross-linked hydrogel formulation could be used and would be superior to pre-existing formulas because it would not require purification post cross-linking. As described above, supplemental components 106 could be added to the binding matrix 102 such as, but not limited to, steroids, NSAIDS, analgesics, growth factors, and supplemental lubricious materials.

Tyramine Cross-Linked Biopolymer: Coatings

An additional application of the described delivery system 100 could be as a coating, wherein hyaluronan is incorporated into the binding matrix 102 prior to use of the delivery system 100 on catheters, as illustrated in FIG. 10, surgical devices, organs that require preservation, as illustrated in FIG. 12, implantable sensors, as illustrated in FIG. 11, artificial hearts, and artificial blood vessels. Incorporation of hyaluronan prior to placement on the surface of a device is important, because cross-linking in place on a surface may reduce particulate generation during manufacturing. Hyaluronan is present in the extracellular matrix, synovial fluid, and vitreous jelly of the eye. It is extremely hygroscopic, so it will attract water and give tissue a plump feel. It is extremely lubricious and plays an important role in lubricating tissue surfaces such as joints, tendon-tendon sheaths, and eyes. Hyaluronan is optically clear and, hence, is one of the main components of the vitreous jelly of the eye. Finally, hyaluronan acts as a barrier to tissue cells, thereby, in some instances, preventing scar tissue formation. For example, hyaluronan prevents tissue cells from entering the space occupied by high concentration masses of hyaluronan, and, by preventing tissue cells from entering the space, it prevents formation of scar tissue. Some bacteria, such as *streptococcus*, cloak themselves in a thick hyaluronan coat so that the immune system cannot reach the cell wall and begin attacking the infecting bacteria early in the infection. Similarly, hyaluronan coatings could be used to protect, lubricate, and resist fouling of surfaces that it coats.

In addition to the various formulations of hydrophilic and lubricious coatings that catheters and wires are already coated by, they could also be coated by one embodiment of the disclosed binding matrix 102 that includes hyaluronan, as illustrated in FIG. 10. This THA-based binding matrix 102a coating could be loaded with pharmaceuticals and bioactive materials (for example, stem cells, biological materials to prevent spasms) 106 prior to cross-linking and coating. Once coated (for example, using covalent bonding to the surface of the catheter), the THA-based binding matrix 102a can be cross-linked and can provide an eluting space within the blood stream. Additional layers of the THA-based binding matrix 102a could also be added on top of the initial THA-based binding matrix 102a layer. Drugs and bioactive materials 106 can be eluted during a procedure for various benefits (for example, to generate a vascular response). In some embodiments, the entire catheter can be coated, which will help prevent arteries from responding to being damaged. In other embodiments, the coating could be limited to specific sections of the catheter, such as its working length. Catheters can be designed to include detachable sections, wherein these sections are intentionally left in the vasculature or neighboring tissues. Therefore, a protective, THA-based binding matrix 102a coating on the section of the catheter left in the vaculature or tissue could be beneficial to the patient.

Surgical devices used to manipulate tissues could be coated, post sterilization, with a THA-based binding matrix 102a to create a protective and lubricious surface that can protect tissues from abrasion and sticking of the device during use. Clamps, retractors, ports, etc. are examples of devices that could be coated with a THA-based binding matrix 102a to protect tissues during surgery.

In some embodiments, the disclosed THA-based binding matrix 102a could be used in a delivery system 100 for use on organs. More specifically, organs harvested for transplant often have a limited time available for transport and examination prior to implant because the harvested tissues can begin to dry on their exterior surfaces and then may not have good $O_2$ exchange. To combat those problems, the organs can be coated in the delivery system 100 having the THA-based binding matrix 102a to protect their exterior surfaces from desiccation and to enhance $O_2$ transport into the tissues. As with previous disclosures, the binding matrix 102 can be loaded with components 106 that enhance the health and viability of the tissues. The thick nature of the delivery system 100 having the cross-linked binding matrix 102 can keep it in place on the surface of the tissues.

The THA-based binding matrix 102a can also be used in the delivery system 100 for use on organs during procedures, as illustrated in FIG. 12, to prevent connective tissue formation. More specifically, during certain procedures or surgeries, surgeons may grab and move tissues or organs around in order to access needed areas of the body. This movement can promote scar tissue formation on the surfaces of these corresponding tissues or organs 108a, which, in the case of intestines, can cause pain or bowel obstructions.

The disclosed delivery system 100 could also help with implanted sensors, as illustrated in FIG. 11, which often quickly foul after implantation, thereby changing the rate of diffusion for the variable being measured and preventing accurate readings of the variable the sensor was implanted to monitor. The delivery system 100 having the THA-based binding matrix 102a not only protects the sensor surface from fouling and prevents formation of scar tissue around the sensor, it has the same mass transport and diffusion properties of tissue. Therefore, proteins, hormones, or small molecules that are being monitored by the sensor could move, unhindered, across the THA-based binding matrix 102a coating and the sensor could provide an accurate measurement.

Artificial hearts are challenging devices since the flow characteristics may cause the blood cells to rupture and cause a clot. The delivery system 100 having the THA-based binding matrix 102a could be used as a coating on an artificial heart to reduce shear forces near the wall surface. Further, the binding matrix 102 could be impregnated with collagen, which would promote endothelial cell migration into the delivery system 100 and create a vessel wall-like coating. The delivery system 100 having the THA-based binding matrix 102a could also prevent fouling of the surface and creation of thrombosis.

As mentioned above, the disclosed delivery system 100 could be used, in some embodiments, on artificial blood vessels; on a bicomponent fiber or cord with a collagen/protein based outer annulus with an sodium hyaluronate cord impregnated with endothelial or stem cell tissue; on skin; in combination with antibiotics, antifungals, growth factors, nutrients and living tissues added to or impregnated within the binding matrix 102; as a plug to fill an annular space, such as a blood vessel or fistula (for example, arteriovenous fistula, anal fistula, and obstetric fistula), or to fill diverticula. It could be used for arteriovenous malformation, for aneurysms, for cerebral spaces, as aortic back filler, as a left atrial appendage, for solid tumors, or for uterine fibroids.

For solid tumors, the delivery system 100 could be inserted at main feeder arteries to occlude the tumor. In some embodiments, the delivery system 100 could include clot-promoting agents. It could also incorporate chemotoxic compounds, monoclonal antibodies targeting tumor specific antigens, apoptosis signals (for example, fas receptor, caspases, and Bcl-2 inhibitors), osmotic disruptors, radio frequency absorptive particles, free radical generators (for example, $TiO_2$ with ionizing radiation), and immunogenic compounds/promoters.

An additional use of the delivery system 100 is as an embolic gel with clot promoting components. For example, a binding matrix 102 with high osmolality components can cause surrounding vessels to spasm and contract tightly. When the contracted state is maintained for an extended period of time (for example, several minutes), blood flow to a solid tumor can be blocked and downstream tissues can die. A chemotoxic agent may be added to the binding matrix 102 and/or drug reservoirs 104 that can elute into the surrounding tissues 108a and provide a locally high concentration of the chemotoxic compound. This can increase the likelihood that cancerous tissues nearby will die while preventing systemic effects from generalized high doses of chemotoxic agents or compounds.

Another example of clot promoting components is a procoagulant component. Procoagulant components can be added to the delivery system 100 (for example, to a high osmolality binding matrix 102 or to a standard binding matrix 102) and can elute from the embolic delivery system 100 and cause a clot to form.

The delivery system 100 could also be used as an embolic mass to occlude a uterine fibroid. As with use for solid tumors, the binding matrix 102 or drug reservoirs 104 could include clot promoting agents and/or chemotoxic agents for stubborn or diffuse fibroids when direct occlusion is insufficient for fibroid destruction.

Another use for the delivery system 100 as an occluding mass is with fistula and diverticula. A peptide-based binding matrix 102 can promote macrophage migration and sclerotic tissue formation. In some embodiments, the binding matrix 102 or drug reservoirs 104 could include endothelial cells with or without stem cells for tissue formation and occlusion.

Tyramine Cross-Linked Biopolymer: Tissue Engineering

In addition to the above-described uses, the disclosed delivery system 100 could be used for in-vivo or in-vitro tissue engineering. Examples of in-vitro tissue engineering include 3D autograft, 3D xenograft, 3D stem cells, 3D combination of autograft and xenograft tissues (for example, xenograft islet cells in combination with collagen and autograft stem cells to promote vessel formation around xenograft cells), 2D bladder, 2D skin, 2D cannula, neural tubes, collagen nested geometry, and lyophilized and ground stomach or bladder lining.

Examples of 3D autograft that involve the disclosed delivery system 100 include harvested islet cells. More specifically, after harvesting host pancreatic tissue or a combination of pancreatic and mesenchymal stem cells from fat tissue, the harvested cells could be loaded into a collagen shell of cadaver or pig pancreas or a 3D printed scaffold. Stem cells could work with the host tissue to create new islet cells in a scaffold that includes nested geometries that mimic the spacing, void size, and density of a pancreas cell scaffold. The binding matrix 102 of the delivery system 100 could be used as a THA coating to protect the scaffold and new islet cells.

In some embodiments, the delivery system 100 could also be used as a cellulose shell in a cylinder for mechanical protection, or it could be injected as globules or particle fragments less than 1.5 mm diameter. More specifically, one way to protect xenografts is to embed them within a cellulose shell that is comprised of thin wall, cellulose, straw-like tubes that prevent the host tissues from attacking them, wherein the shell has a high mechanical strength. One limitation of the cellulose shell is limited diffusion of nutrients and oxygen into the graft and limited diffusion of waste products out of the graft. To resolve this limited diffusion, some embodiments of the disclosed technology incorporate the delivery system 100 into the cellulose shell. The hydrogel particles paired with the hydrogel can be small and will not need a high strength shell. Additionally, diffusion of materials in and out of the graft is much easier when using the delivery system 100. One drawback of the delivery system 100 is that its components can absorb into the body and, therefore, may not hold the xenograft cells in the desired location for a long period of time if it does absorb. Therefore, a combination of the cellulose shell and the delivery system 100 can be used to enable protection from attacks by host tissues and endurance in a desired location.

Similar to 3D autograft, the disclosed delivery system 100 could help with 3D xenograft. The THA-based binding matrix 102a can protect cells, such as islet cells from a pig, a human donor, or a human cadaver, from the host's immune system. In some embodiments, the binding matrix 102 could be combined with hepatic stellate cells to form longer-term viability. The cells could then be concentrated and 1.5 mm diameter maximum solid rods (for example, cellulose shell) could surround the cells encapsulated within the THA-based binding matrix 102a. A cellulose shell can provide the delivery method and mechanical protection for the delivery system 100. The composition could be modified by using a degrading shell (i.e., cat gut), and the THA-based binding matrix 102a could protect the xenografts from the host immune system. In moderately vascularized tissue, a 1.5 mm maximum diffusion distance may be enabled (for example, for $O_2$, nutrients, waste removal, etc.). Some embodiments could modify the composition to present using injection without a cellulose shell (i.e., a denser gel particle). In one embodiment, there is at least a thirty-day viability minimum. In a preferred embodiment, there is at least a twelve-month viability minimum. In one embodiment, an alternative would be to use an embodiment of the delivery system 100 having a dense, THA-based binding matrix 102a to surround the cells. The delivery system 100 having a dense, THA-based binding matrix 102a could allow injection via a small diameter needle while allowing material to flow into the site and to enter into the interstitial spaces.

In addition to islet cells, thyroid cells from a cadaver donor could be used in a xenograft after they are harvested and sorted in the host tissue. In cases of thyroid cancer, excessive nodules, or traumatic neck injury, living thyroid cells could be harvested from a cadaver or donor, and a xenograft could be encapsulated as described for the islet cells above. The living tissue could be allowed to produce hormones, and hormone levels found in tissue could be monitored. This is beneficial because biological systems are much better at controlling dosage and timing of dosage than artificial systems.

Similar to the methods disclosed for islet and thyroid cells, pituitary cells from living tissue can be harvested or donated and can be grafted in cases where there is insufficient growth hormone or lutenizing hormones due to damage, genetic defect, or other cause. Benefits would be to prevent syndromes, growth rate abnormalities, and to complete grafts in a well-controlled manner. In the case of dwarfism, a growth hormone could be supplied directly from the tissues. In the case of gigantism, the pituitary can be inactivated via radiation or surgical means and then living tissue can be delivered using the delivery system 100 to provide growth hormones at an acceptable rate.

To create 3D stem cells, a three dimensional tissue scaffold can be created by laying down thin layers of the delivery system 100, one on top of the next, with each layer containing a specific geometry that would mimic the target tissue type in both microscopic and macroscopic geometry. Different materials could also be used in different regions of the layers to elicit a desired response from the surrounding tissues. One example of a desired response is to encourage stem cell migration or migration of macrophages to nucleating sites that can draw in new stem cells and start the wound healing process with the end result being a functioning and fully differentiated desired tissue type. In another embodiment, the method would include creating the voids and macroscopic geometry using an easily dissolved material such as a paraffin or low molecular weight polymer and allowing the binding matrix 102 to fill the interstitial spaces and then cross-link in place. Once the polymer or filler material is removed through dissolution, then the hydrogel scaffold will be left behind as a negative space rendering of the originally desired geometry. This would allow for nested geometries (annular vessels, dense and less dense regions, etc.), as illustrated in FIG. 9. Although both methods could be used to create a macro structure, different approaches may be optimal for one method over the other.

In some embodiments, they delivery system 100 could be used to create simple bladder tissue by allowing the binding matrix 102 to act as a basal layer to build upon with bladder endothelial cells. Surface geometry can be set up to promote tissue growth, and the binding matrix 102 can be supplied with nutrients and growth promoters that would allow the tissue to grow faster than can be currently grown in the lab. Similar to the process described above for 3D stem cells, microscopic and macroscopic geometry can be created to promote growth or more complex and mature bladder walls.

In some embodiments, the delivery system 100 can be used to create neural tubes such as, but not limited to, olfactory ensheathing cells or nano tubules. For example, olfactory ensheathing cells of various concentrations can be suspended in the binding matrix 102 and injected into a spinal or nerve bundle site.

Another form of in-vitro tissue engineering using the delivery system 100 is for collagen-nested geometry. In some embodiments, the collagen form of the binding matrix 102 can be applied much like a 3D printer in successive layers to create a collagen network similar to the extracellular matrix found in a target organ. As this binding matrix 102 is seeded with stem cells, the undifferentiated cells can take the shape of the collagen matrix and, due to the mechanical form, begin to transform into differentiated cells of this target organ.

Lyophilized, or free-dried, stomach, bladder, or sub-dermal tissue lining, is a further form of in-vitro tissue engineering that can be completed using the disclosed delivery system 100. Historically, freeze-dried powder of a bladder has, in some situations, been applied to the surface of an open wound to advance a healing cell front. Theoretically, tissue found in the stomach lining, bladder lining, and basal dermal layers contain growth factors that promote a high rate of tissue growth since these are tissues that are eroded quickly and must continue growing to replace the eroded/abraded surface. These growth factors, likely in combination with a collagen scaffold created by the rehydrated powder, allow the surrounding tissue from a wound to migrate into the scaffold, begin growth, and start growing outward to fill in the wound. Surrounding tissues 108a likely have control factors that cause the new cells to differentiate and create the proper tissue type in the correct positions. This can result in situations similar to how a lizard can regrow tails and amphibians can regrow limbs. In this application, the powdered tissue can be incorporated into the binding matrix 102 in a dense and firm formulation to protect the wound from infection. This formulation can seal the edges and create a robust matrix into which the new cells can migrate and start new tissue growth 108b. In one embodiment, the delivery system 100 can be applied in small sheets to allow the cells to build from the basal tissue layer 108a and create the new tissue 108b in the correct location. Without tensegrity and/or cell signaling from surrounding tissues, a large limb growth or replacement may have to be grown in small thin sheets that are applied daily until the limb has regrown completely. Similarly, this method could be used to heal large wounds in which a mass of tissue is missing and the body may have a large gap, or opening, or may have a large tunneling wound.

The various embodiments described above are provided by way of illustration only and should not be construed to limit the claims attached hereto. Those skilled in the art will readily recognize various modifications and changes that may be made without following the example embodiments and applications illustrated and described herein and without departing from the true spirit and scope of the following claims.

What is claimed is:

1. A hydrogel-based drug delivery vehicle for delivering a drug to a wound comprising:
   a) a first hydrogel matrix comprising a solvent and a plurality of chains of a first biopolymer dissolved in the solvent, the first biopolymer having a structure:

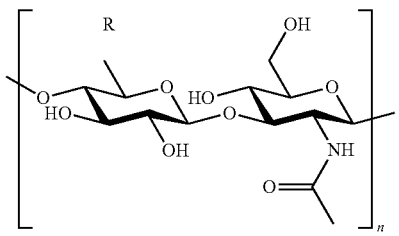

wherein n is an integer greater than or equal to 220;
   wherein R is COOH or tyramine and wherein 1.5 mol % of R of the first biopolymer is tyramine;
   wherein the first hydrogel matrix comprises from 1 mol % to 2 mol % of the first biopolymer and water as the solvent; and
   wherein the solvent comprises water;
   b) a plurality of drug reservoirs dispersed throughout the first hydrogel matrix; and
   c) a cross-linking agent, wherein the cross-linking agent cross links tyramines within the first hydrogel matrix.

2. The hydrogel-based drug delivery vehicle of claim 1, wherein the drug reservoirs comprise an analgesic.

3. The hydrogel-based drug delivery vehicle of claim 2, wherein the analgesic is bupivacaine.

4. The hydrogel-based drug delivery vehicle of claim 1, wherein each of the plurality of drug reservoirs comprise:
   i) a second hydrogel matrix comprising a solvent and a plurality of chains of a second biopolymer comprising:

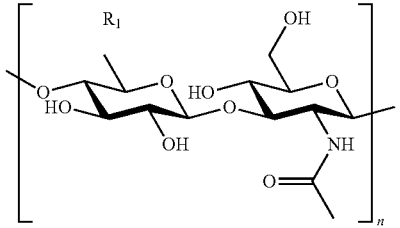

wherein n is an integer greater than or equal to 220;
   wherein $R_1$ is COOH or tyramine and wherein more than 1.5 mol % of R1 of the second biopolymer is tyramine;
   wherein a concentration of the second biopolymer in the second hydrogel matrix is greater than a concentration of the first biopolymer in the first hydrogel matrix and wherein the solvent comprises water; and
      ii) an analgesic agent dispersed within the each of the plurality of drug reservoirs.

5. The hydrogel-based drug delivery vehicle of claim 4, wherein the analgesic is bupivacaine.

6. The hydrogel-based drug delivery vehicle of claim 1, further comprising horseradish peroxidase and wherein the cross-linking agent is hydrogen peroxide.

7. The hydrogel-based drug delivery vehicle of claim 1, wherein the osmolality of the first hydrogel matrix is higher than physiologic osmolality of the wound.

8. The hydrogel-based drug delivery vehicle of claim 7, wherein the osmolality of the first hydrogel matrix is higher than 295 mOsm/Kg.

9. The hydrogel-based drug delivery vehicle of claim 7, wherein the first hydrogel matrix swells upon implantation into the wound.

10. The hydrogel-based drug delivery vehicle of claim 9, wherein the first hydrogel matrix absorbs fluid from surrounding tissue upon implantation into the wound.

11. The hydrogel-based drug delivery vehicle of claim 9, wherein the first hydrogel matrix inhibits wound bleeding upon implantation into the wound.

12. The hydrogel-based drug delivery vehicle of claim 1 that is loaded in a syringe.

13. A hydrogel-based drug delivery vehicle for delivering a drug to a wound comprising:
   a) a first hydrogel matrix comprising a solvent and a plurality of chains of a first biopolymer dissolved in the solvent, the first biopolymer having a structure:

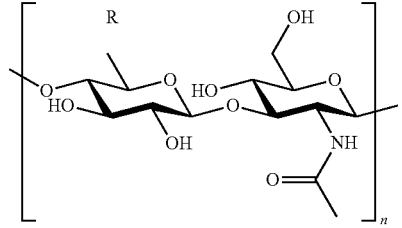

wherein n is an integer greater than or equal to 220;
   wherein R is COOH or tyramine and
   wherein 1.5 mol % of R of the first biopolymer is tyramine; and wherein the first hydrogel matrix comprises from 0.5 mol % to 1.5 mol % of the first biopolymer and water as the solvent; and wherein the osmolality of the first hydrogel matrix is higher than 295 mOsm/Kg;
   b) a plurality of drug reservoirs dispersed throughout the first hydrogel matrix, each of the plurality of drug reservoirs comprising:
      i) a second hydrogel matrix comprising a solvent and a second biopolymer comprising:

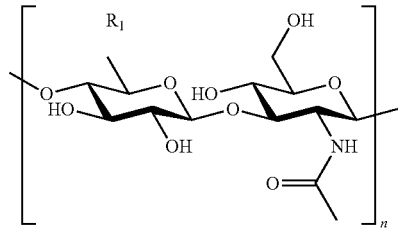

wherein n is an integer greater than or equal to 220;
   wherein $R_1$ is COOH or tyramine and
   wherein more than 1.5 mol % of R1 of the second biopolymer is tyramine;

wherein a concentration of the second biopolymer in the second hydrogel matrix is greater than a concentration of the first biopolymer in the first hydrogel matrix and wherein the solvent comprises water; and
    ii) an analgesic agent dispersed within the each of the plurality of drug reservoirs; and
c) a cross-linking agent, wherein the cross-linking agent cross links tyramines within the first and second hydrogel matrix.

14. The hydrogel-based drug delivery vehicle of claim 13, wherein first hydrogel matrix swells upon implementation into the wound.

15. The hydrogel-based drug delivery vehicle of claim 14, wherein the first hydrogel matrix absorbs fluid from surrounding the cross-linking agent is hydrogen peroxide.

16. The hydrogel-based drug delivery vehicle of claim 14, further comprising horseradish peroxide and wherein the cross-linking agent is hydrogen peroxide.

* * * * *